United States Patent [19]
Sugiura et al.

[11] Patent Number: 6,034,766
[45] Date of Patent: Mar. 7, 2000

[54] OPTICAL MEMBER INSPECTION APPARATUS

[75] Inventors: Masayuki Sugiura, Saitama-ken; Kiyoshi Yamamoto, Tokyo; Taichi Nakanishi, Saitama-ken, all of Japan

[73] Assignee: Asahi Kogaku Kogyo Kabushiki Kaisha, Tokyo, Japan

[21] Appl. No.: 09/035,055

[22] Filed: Mar. 5, 1998

[30] Foreign Application Priority Data

Mar. 5, 1997 [JP] Japan ..................................... 9-050760
Mar. 5, 1997 [JP] Japan ..................................... 9-050761

[51] Int. Cl.[7] .............................. G01N 21/00; G01B 9/00
[52] U.S. Cl. .................................... 356/239.1; 356/239.2; 356/124
[58] Field of Search .............................. 356/239.1, 239.2, 356/338, 124

[56] References Cited

U.S. PATENT DOCUMENTS 5,216,481  6/1993  Minato .
5,767,961  6/1998  Nishikawa et al. .................. 356/239.1
5,828,500  10/1998  Kida et al. ............................ 356/239.1
5,835,207  11/1998  Sugiura et al. .......................... 356/124
5,847,822  12/1998  Sugiura et al. .......................... 356/124

FOREIGN PATENT DOCUMENTS 9-15159   1/1997  Japan .
95/01558  1/1995  WIPO .

Primary Examiner—Frank G. Font
Assistant Examiner—Zandra V. Smith
Attorney, Agent, or Firm—Greenblum & Bernstein, P.L.C.

[57] ABSTRACT

An optical member inspection apparatus is disclosed. A light shielding plate functions to cast a shadow region so that a line sensor receives an image producing a particular defined image data output, generally speaking a dark image representing an absence of light from an illuminator. When an inspection target optical member is inserted in the light path to intersect that shadow region, the line sensor produces the same image data in the event that there is no defect in the optical member. However, a defect in the optical member will enable light from outside that shadow region to be diffused to impinge on the line sensor thereby producing a change in the image data output. Evaluation of the change in the image data output can provide an indication of the degree of defectiveness.

26 Claims, 36 Drawing Sheets

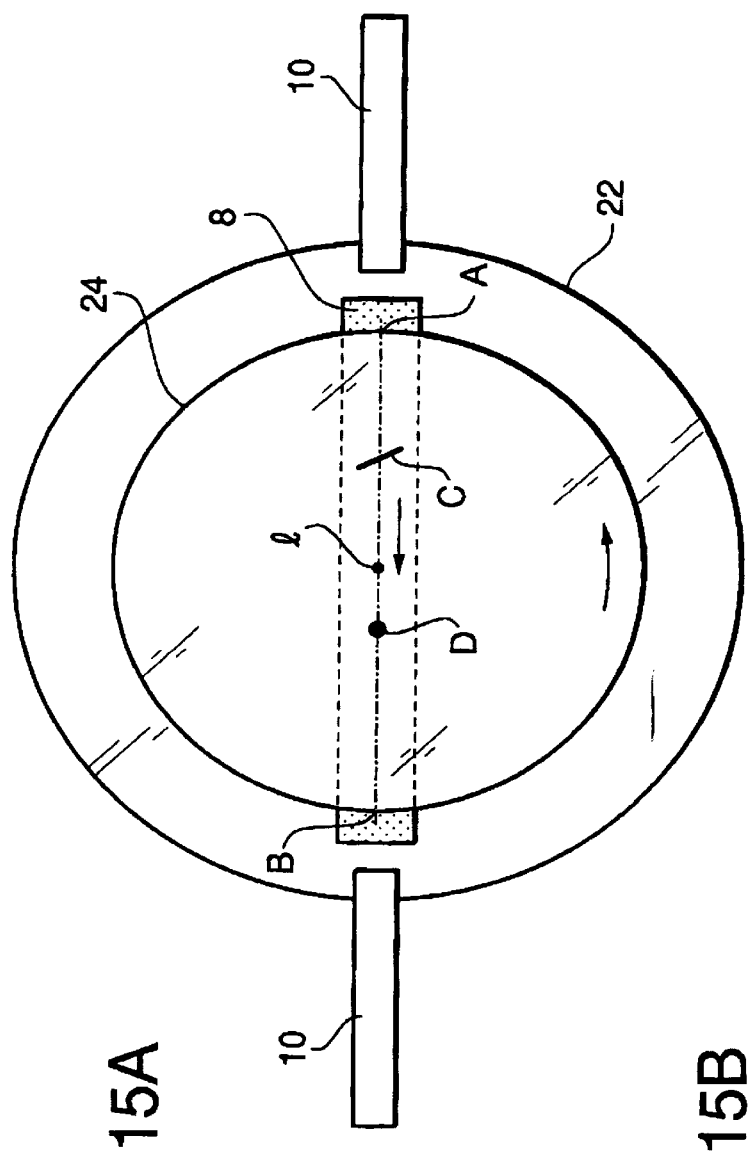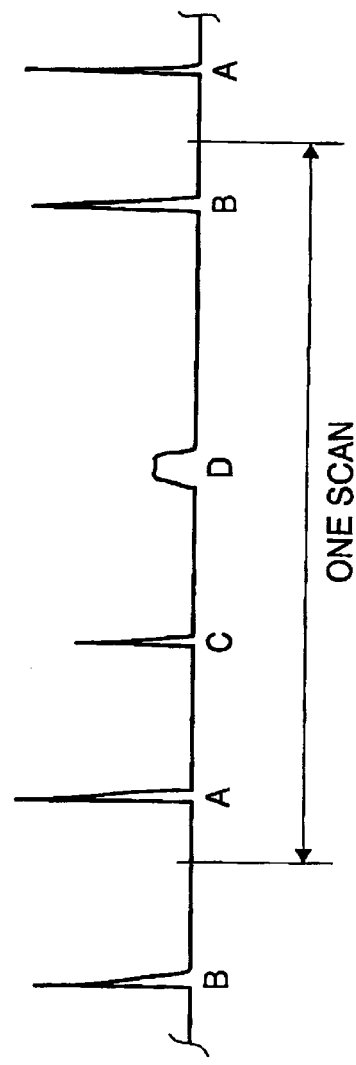
FIG. 15A
FIG. 15B

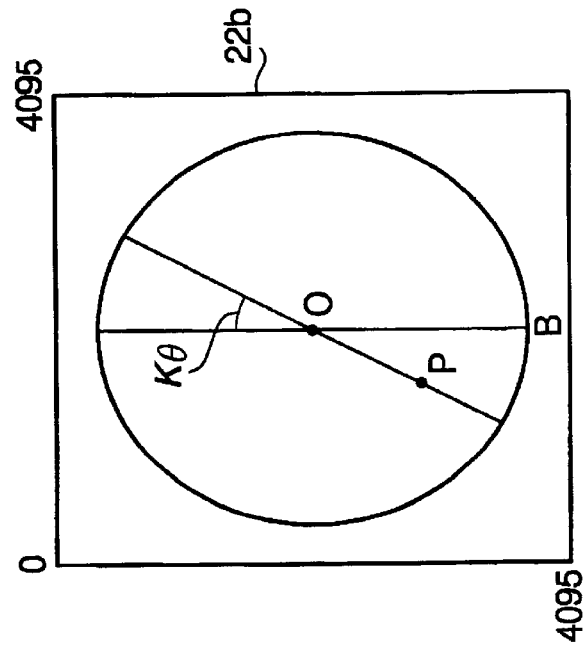
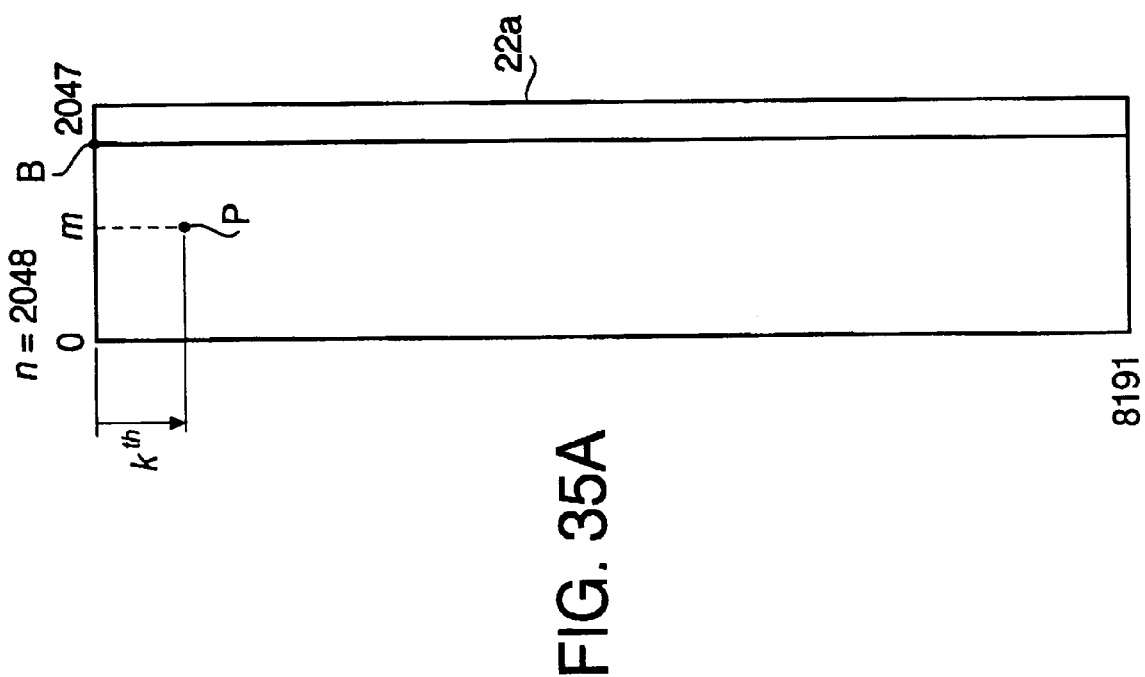
FIG. 35B
FIG. 35A

OPTICAL MEMBER INSPECTION APPARATUS

BACKGROUND OF THE INVENTION

The present invention relates to an optical member inspection apparatus for detecting an optical defect, such as an abnormality in shape or the like, in an optical member such as a lens or the like which may be made by a plastic injection process.

An optical member such as a lens or a prism, etc., is generally designed such that light incident thereupon is refracted regularly, advanced in parallel, converged onto a point or line, or diverged. However, if the optical member contains therein a foreign substance such as a cotton waste or the like (so-called "fuzz"), due to a defective formation thereof, or if the optical member is scratched during handling thereof by an operator, or it foreign matter is affixed to the surface of the optical element, the light incident upon the optical member can be disturbed, thus resulting in a failure to obtain a desired optical property.

Previously, sensory tests relying upon an operator's eyesight have been carried out using a fluorescent lamp or a light source for a slide projector.

In an inspection using a fluorescent lamp or a light source for a slide projector, an optical member is illuminated with light emitted from the lamp or the light source, and the surface of the optical member is observed by an operator outside of the optical path so as to find a detective portion on the surface of the optical member by checking the level of luminance brightness, taking into consideration light reflection, transmission, refraction or the like.

However, such a sensory inspection relying on an operator's eyesight is subjective, there being no definite objective criterion to discriminate a defective product from a non-defective product. Consequently, in the case that the inspection is executed by more than one inspector, the judgment (inspection result) may vary depending upon the inspector. Namely, the same product may be judged "defective" by one inspector and "non-detective" by another inspector. Consequently, a 'non-defective' product may unnecessarily be wasted or destroyed. Also, if a defective product is included in a batch of non-defective products, the overall quality of the whole batch is reduced. Moreover, even where the same inspector checks the products, the criterion applied by that inspector tends to become more strict through experience and practice, so that the probability that a non-defective product is mistakenly judged to be a defective product can increase.

Finally, the aforesaid test relies on human operation and is accordingly relatively slow.

SUMMARY OF THE INVENTION

It is therefore an object of the present invention to provide an optical member inspection apparatus capable of judging the quality of an optical member in accordance with an objective criterion, and preferably of being inspected rapidly and reliably.

The present invention provides an optical member inspection apparatus for detecting an optical defect of an inspection target optical member, comprising:

an imaging lens;
a line sensor arranged at a position conjugate to said inspection target optical member with respect to said imaging lens;
an illuminator for illuminating said inspection target optical member;
a light shielding member interposed between said inspection target optical member and said illuminator, for shielding an optical path of light which would be incident upon said line sensor after transmitting through said inspection target optical member;
a numerical system which determines a numerical value for an optical image obtained by said line sensor, said numerical value being indicative of said optical defect of said inspection target optical member; and
discrimination system which makes a decision whether said numerical value exceeds a predetermined discrimination reference value.

In the optical member inspection apparatus thus constructed, light from the illuminator which passes through the inspection target optical member and is then incident upon the imaging lens, follows light paths outside those which would be incident upon the line sensor on correct functioning of the inspection target optical member. Thus, illumination light incident upon the imaging lens will not be incident upon the line sensor unless the inspection target optical member has an optical defect. Therefore, the image obtained by or on the line sensor is dark as a whole where there is no defect.

On the contrary, in the case where there is an optical defect in the imaging inspection region of the inspection target optical member, the illumination light incident upon the imaging region diffuses due to the optical defect. Then, when a part of the diffused light is incident upon the imaging lens, the diffuse light converges on the line snesor; for this reason, a bright image of the optical defect is obtained by means of the line sensor. Therefore, a bright portion corresponding to the optical defect appears in the obtained image.

In the present invention, the inspection target optical member may be transparent optical members such as a lens, a prism, a plane-parallel plate or the like. The inspection target optical member may be formed of glass or molded of plastic. The aforesaid optical defect of the optical members includes defects caused on the surface of the optical member and in the interior thereof, e.g. scratches, dirt, dust and the like on the surface are possible defects on the surface of the optical member, whereas fuzz, cracks, bubbles and the like caused in the interior are possible defects within the optical member.

The numerical system may correspond to an area of a bright portion indicative of the optical defect of the optical member in the image, and may be calculated from a width, a luminance, and/or a value multiplied from these.

With respect to the discrimination system, if the numerical value determined by the numerical system includes a plurality of elements, all values of these elements may be compared with a discrimination reference value, or only the value of one element depending upon the kind of the optical member to be compared therewith.

The light shielding member prevents light transmitting through the inspection target optical member from being directly incident upon the line sensor. Thus, so long as a sector surrounded by the marginal ray lines of light incident upon the line sensor is shielded, the light shielding member may be arranged anywhere between the diffusion plate and the inspection target optical member. Further, the light shielding member may, of course, have any other shape in its plane so long as at least the aforesaid sector surrounded by the marginal ray lines is shielded.

Therefore, the light shielding member preferably has a narrow strip-like shape in its plane.

Further, even if the line sensor is made long to improve the resolution, the width of the light shielding member is unchanged.

Moreover, the light shielding member may be a light shielding pattern which is printed directly on the surface of the diffusion plate, or may be a plate-like opaque member which is stuck onto the diffusion plate, or may be a light shielding pattern which is printed on the surface of a transparent member independent from the diffusion plate.

Preferably, the line sensor has a scanning direction extending in a fixed direction perpendicular to an optical axis of the imaging lens, and wherein the light shielding member has a shape extending in the same fixed direction.

Preferably, magnification of the imaging lens is adjusted so that the image of the entire width of the inspection target optical member is obtained by means of the line sensors.

Preferably, the optical member inspection apparatus further includes a transfer system to move the inspection target optical member in a direction perpendicular to the scanning direction of the line sensor, and wherein the line sensor obtains an image of the inspection target optical member at different positions, and outputs an image data for each one line. With this construction, if the line sensor is employed, it is possible to make an inspection with respect to the overall region of the inspection target optical member.

Further preferably, the optical member inspection apparatus includes an auxiliary illumination unit for illuminating a portion of the inspection target optical member from a side of the light shielding member in the fixed direction. With such a construction, even in the case where the length of the longitudinal direction of the light shielding plate is longer than the width of the inspection target optical member, it is possible to illuminate the imaging region of the inspection target optical member from the longitudinal direction of the light shielding plate Therefore, whatever the orientation of the defect portion, it is possible to direct diffused illumination light onto the defect portion, and to make it incident upon the imaging lens.

Preferably, the numerical system reconstructs image data corresponding to the entire inspection target optical member on the basis of the image data for each one line outputted from the line sensor, and measures a number of pixels having a luminance larger than a predetermined threshold value in the image data.

The optical member inspection apparatus may further include a rotating unit which rotates the inspection target optical member around an optical axis of the imaging lens, magnification of the imaging lens being adjusted so that the image of the entire region of the inspection target optical member in a diameter direction thereof is obtained by means of the line sensor, and the line sensor obtains an image of the inspection target optical member at different positions and outputs image data for each one line.

Preferably, besides the above construction, the optical member inspection apparatus may further include a rotating unit which rotates the inspection target optical member around a rotating axis offset from the optical axis of the imaging lens, magnification of the imaging lens being adjusted so that the image of a region extending from the rotating axis to an outer edge of the inspection target optical member is obtained by means of the line sensor, and the line sensor may obtain an image of the inspection target optical member at different positions and outputs image data for each one line.

The numerical system measures a length of a portion of image data having a luminance larger than a predetermined threshold value in the image data for each one line outputted from the line sensor.

Further, the numerical system reconstructs an image data of a polar coordinate system corresponding to the entire inspection target optical member on the basis of the image data for each one line outputted from the line sensor, converts the image data of polar coordinate system into an image data of a rectangular coordinate system, and measures a number of pixels having a luminance larger than a predetermined threshold value in the image data of the rectangular coordinate system.

Furthermore, the rotating unit may constitute a unit for rotating the inspection target optical member around an optical axis of the inspection target optical member. With this construction, even in the case of inspecting an optical member such as lens, having a refraction power in the diameter direction thereof around the optical axis, the shadow of the light shielding plate is not moved on the imaging surface of the line sensor so that the image capturing can be carried out while fixing the line sensor.

The light shielding member can have a strip-like shape which is gradually expanded from a portion intersecting the optical axis of the inspection target optical member to an end portion thereof. With this construction, in the position in the vicinity of the optical axis of the optical member, an incident angle of the illumination light striking on the defect portion of the inspection target optical member becomes small; therefore, this serves to increase the possibility that the illumination light diffused on the defect portion is incident upon the imaging lens. On the other hand, in the position in the vicinity of the peripheral edge of the optical member, an incident angle of the illumination light striking on the defect portion of the inspection target optical member becomes large; therefore, this serves to decrease the possibility that the illumination light diffused on the defect portion is incident upon the imaging lens. In other words, it is possible to make high a defect detection sensitivity in the vicinity of the optical axis of the optical member, and to make low the defect defection sensitivity in the vicinity of the peripheral edge thereof.

From a different aspect, the present invention provides an optical member inspection apparatus for detecting an optical defect of an inspection target optical member, comprising:

an imaging lens;

an image rotator which is arranged on an object side of said imaging lens so as to be freely rotatable around an optical axis of said imaging lens;

a fixing member for fixing said inspection target optical member on said optical axis on a side opposite to said imaging lens via said image rotator;

a line sensor which is arranged on a position conjugate to said inspection target optical member fixed on said fixing member with respect to said imaging lens;

a diffusion plate which is arranged on a side opposite to said image rotator via said inspection target optical member fixed on said fixing member, and diffuses an illumination light toward said inspection target optical member;

a light shielding member which is interposed between said diffusion plate and said inspection target optical member, and shields an optical path of an illumination light which is incident upon said line sensor after transmitting through said inspection target optical member and being incident upon said imaging lens;

a first rotating mechanism for rotating said light shielding member around said optical axis;

a second rotating mechanism for rotating said image rotator so that a shadow of said light shielding member formed by said imaging lens always covers said line sensor, in synchronism with rotation of said light shielding member by said first rotating mechanism;

numerical system which determines a numerical value for an optical image obtained by said line sensor; and discrimination system which makes a decision whether said numeral value exceeds a predetermined discrimination reference value.

In the optical member inspection apparatus thus constructed, the light shielding member is directed to a direction parallel with the line sensor direction in the initial state. Among illumination lights diffused from various portions of the diffusion plate, a light ray, which travels to a direction incident upon the line sensor after transmitting through the inspection target optical member and being incident upon the imaging lens, is shielded by means of the light shielding member interposed between the diffusion plate and the inspection target optical member. In this initial state, since the image rotator is also situated in the initial position, the shadow of the light shielding member covers the line sensor in spite of the rotation of the image rotator. However, in the case where there is an optical defect in a line-like region intersecting the optical axis parallel with the light shielding member in the inspection target optical member, the illumination light, which passes through the side of the light shielding member and is incident upon the line-like region, diffuses due to the optical defect.

Then, when a part of the diffused light is incident upon the imaging lens, the diffused light converges on the line sensor, so that a bright image of the optical defect can be captured by means of the line sensor. Therefore, a bright portion corresponding to the optical defect appears in the image captured by the line sensor. During this imaging, the light shielding member is rotated around the optical axis by means of the first rotating mechanism. Whereupon the second rotating mechanism rotates the image rotator in synchronism with the rotation of the light shielding member. By taking advantage of the rotation, the image rotator rotates a shadow of the light shielding member so as to cover the line sensor. As a result, the optical defect, which exists in the line-like region intersecting the optical axis parallel with the light shielding member after rotation, is captured by means of the line sensor. When the light shielding member and the image rotator rotates in the aforesaid manner, the image of the line-like region captured by the line sensor is rotated. Therefore, during rotation of the light shielding member, the image corresponding to the entire region of the inspection target optical member can be captured.

The image rotator is rotated around the optical axis of the imaging lens, and thereby, the image rotator functions as an optical member for rotating a position of emitted rays with respect to a position of incident rays around the optical axis thereof. Further, the image rotator may be constructed in a manner that the position of emitted rays is made one rotation during one rotation of the image rotator, or the position of emitted rays is made one rotation during a half-rotation of the image rotator.

The diffusion plate may be a light transmitting member illuminated from a rear side thereof, or may be a reflection member illuminated from the surface side thereof.

The first rotating mechanism may solely rotate only light shielding plate, or may rotate the diffusion plate in which the light shielding plate is stuck onto the surface thereof.

The second rotating mechanism may rotate the image rotator in the reverse direction at the same speed as the rotating speed of the light shielding plate by the first rotating mechanism in the case where the position of emitted rays is made one rotation during one rotation of the image rotator. Further, the second rotating mechanism may rotate the image rotator in the reverse direction at a speed which is a half of the rotating speed of the light shielding plate by the first rotating mechanism in the case where the position of emitted rays is made one rotation during a half-rotation of the image rotator.

The image rotator is preferably constructed in a manner that when the image rotator is rotated by a predetermined angle around the optical axis, a position of a ray emitted from the image rotator is rotated by a twice angle of the predetermined angle around the optical axis.

Further, the second rotating mechanism preferably rotates the image rotator at a speed which is a half of a rotating speed of the light shielding member by the first rotating mechanism.

Conveniently, the second rotating mechanism can rotate the image rotator in a reverse direction to the rotating direction of the light shielding member by the first rotating mechanism.

BRIEF DESCRIPTION OF THE DRAWINGS

FIG. 15A is a plan view showing an optical member to be inspected from a position of a line snesor shown in FIG. 14;

FIG. 15B is a graph showing a luminance distribution of image data outputted from a line sensor in the case where there is an optical defect in the optical member to be inspected;

FIG. 35A and FIG. 35B are each a memory map showing image data stored in each image memory shown in FIG. 29;

DESCRIPTION OF THE PREFERRED EMBODIMENTS

Preferred embodiments according to the present invention will now be described below with reference to the accompanying drawings.

Embodiment 1

A first embodiment relates to an optical member inspection apparatus suitable for inspecting an optical member which has no specific optical axis, for example, a plane-parallel plate.

Arrangement of the optical member inspection apparatus

Figure 1:
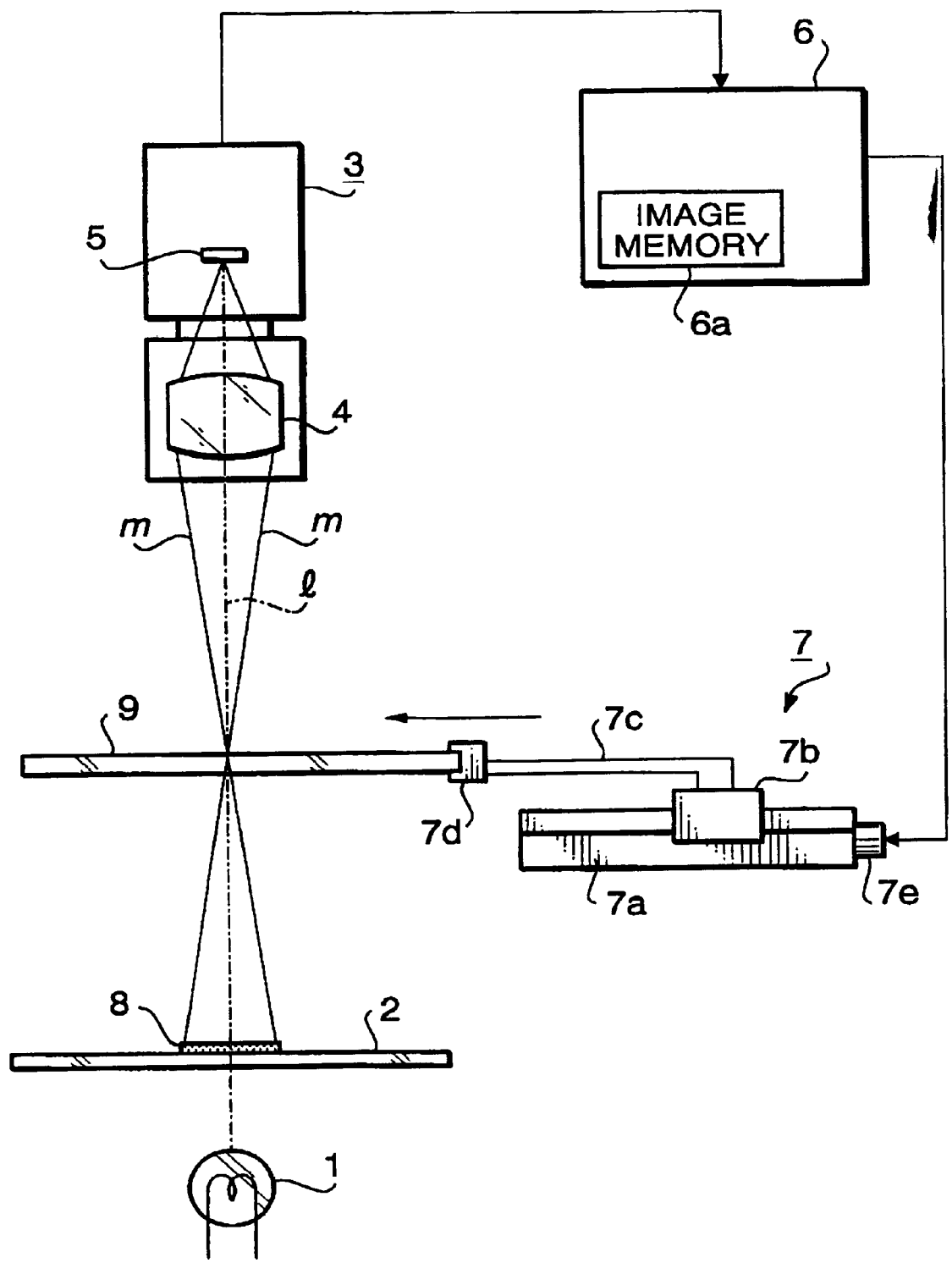
FIG. 1 is a front view schematically showing an optical member inspection apparatus according to a first embodiment of the present invention.
Figure 2:
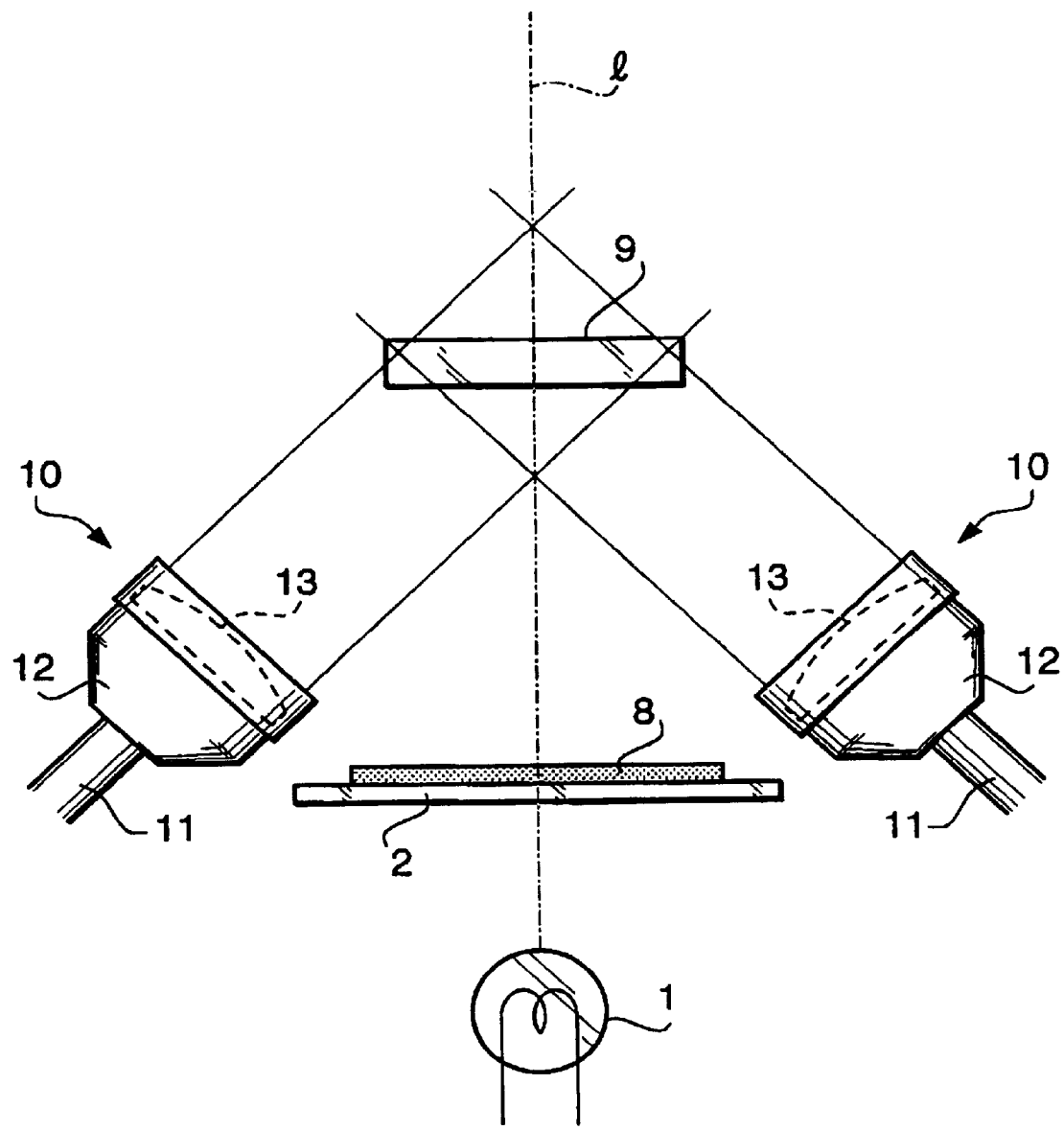
FIG. 2 is a partial side view of the optical member inspection apparatus shown in FIG. 1.

FIG. 1 is a front view schematically showing an optical member inspection apparatus according to a first embodiment of the present invention, and FIG. 2 is a partial side view thereof. As shown in FIG. 1, an optical member inspection apparatus comprises an illumination lamp 1, a diffusion plate 2 and an image pick-up device 3, which are aligned along a common optical axis l.

The image pick-up device 3 comprises an imaging lens 4, which is a positive lens system, and a CCD line sensor 5 which picks up an image formed by light converged by means of the imaging lens 4. In FIG. 1, the line sensor 5 is arranged such that a row of pixels is oriented to a direction perpendicular to the plane of the paper. The pixel row of the line sensor 5 intersects the optical axis l of the imaging lens 4 at a right angle and the center of the row coincides with the optical axis l. The imaging lens 4 can freely reciprocate for focussing with respect to the line sensor 5 in the image pick-up device 3. Further, the image pick-up device 3 itself is mounted on a frame, not shown, of the inspection apparatus in such a fashion as to be able to reciprocate along the optical axis l.

The line sensor 5 captures a line image for each predetermined time (a time interval of sufficient value that electric charge is adequately stored in each pixel), and then, self-scans each pixel in the arranged order of pixels to output electric charge stored at each pixel. Electric charge thus outputted from the line sensor 5 is subjected to a predetermined amplification process and to an A/D conversion process, and thereafter, is inputted to an image processor unit 6 as image data consisting of a luminance signal for one line.

The image processor unit 6 is a processor for making a decision whether an inspection target optical member 9 is non-defective or defective. More specifically, the image processor unit 6 carries out a predetermined image processing with respect to the image data inputted from the line sensor 5, and then, expresses a degree of optical defectiveness of the inspection target optical member 9 as a numerical value. In addition, the image processor unit 6 compares the numerical value with a predetermined discrimination reference value (allowable value), and makes a decision whether the numerical value is under the discrimination reference value or exceeds it. During this image processing, the image processor unit 6 outputs a control signal to a slide table unit 7 to move the inspection target optical member 9 in synchronisation with data output from the line sensor 5. The image processor unit 6 has a built-in image memory 6a for storing image data during the above image processing.

The slide table unit 7 comprises a slide rail 7a, a slider 7b, a driving motor 7e, a boom 7c and a holder 7d. The slide rail 7a is fixed to a frame, not shown, of the inspection apparatus in such a manner as to be perpendicular to the pixel row of the line sensor 5 and to the optical axis l of the imaging lens 4. The slider 7b is slidable on the slide rail 7a. The driving motor 7e drives the slider 7b to slide on the slide rail 7a at a constant speed. One end of the boom 7c is fixed to the slider 7b, while the other end is secured to the holder 7d. The holder 7d detachably holds the inspection target optical member 9. When a control signal is output from the image processor unit 6, the driving motor 7e is rotated thereby so as to move the slider 7b along the slide rail 7a. As a result, the inspection target optical member 9 is moved at a constant speed in a direction perpendicular to the pixel row of the line sensor 5 and to the optical axis l of the imaging lens 4.

Figure 3:
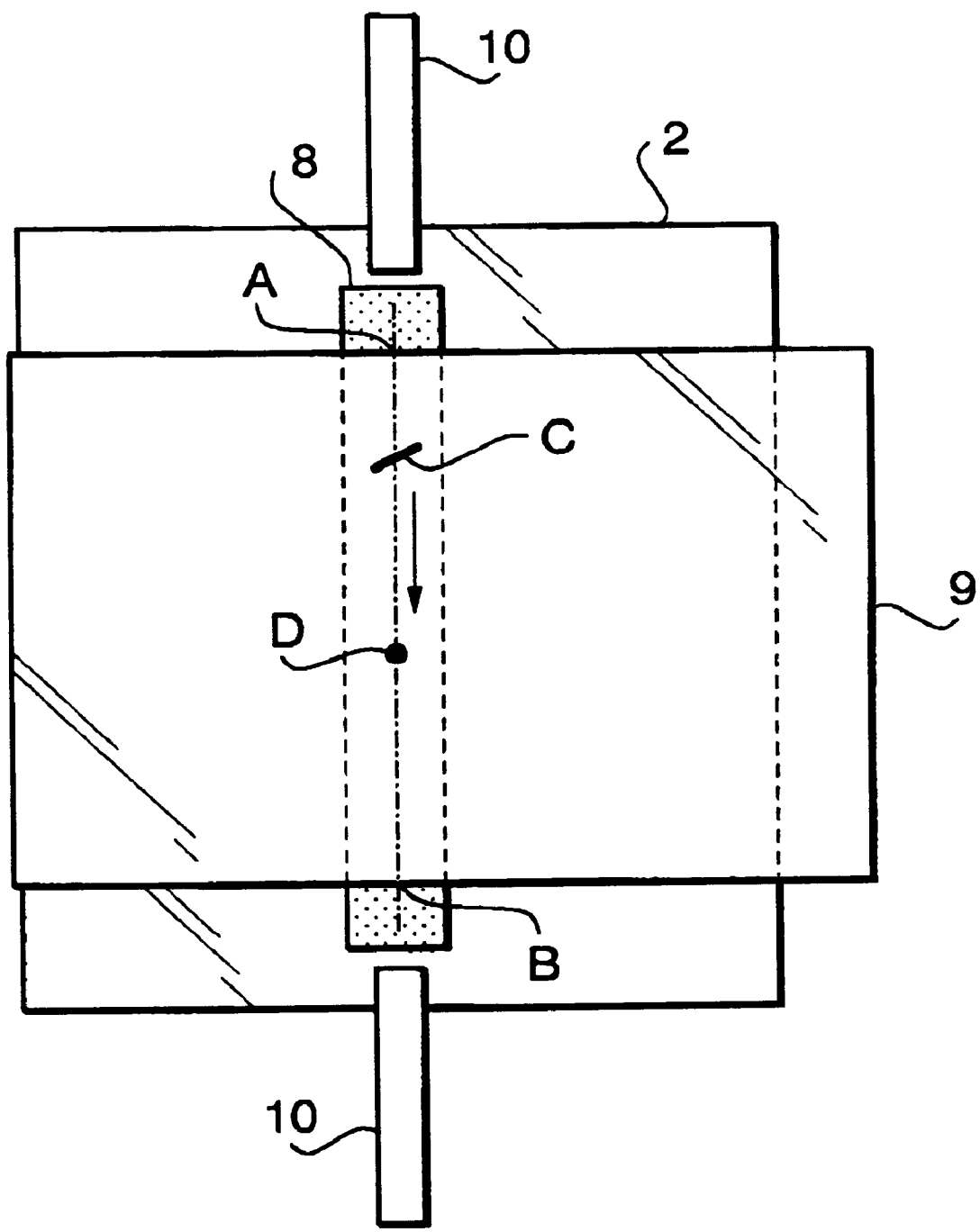
FIG. 3 is a plan view showing an optical member to be inspected from a position of a line sensor shown in FIG. 1.

The inspection target optical member 9 is a plane-parallel transparent plate having a rectangular flat surface as shown in FIG. 3. The inspection target optical member 9 is held and moved by means of the slide table unit 7 such that its shorter side is parallel with the pixel row of the line sensor 5 and perpendicular to the optical axis l of the imaging lens 4 so as to be centralized about that axis.

FIG. 3 is a top plan view showing positional relationships of the inspection target optical member 9 and other components when viewed from a position of the imaging lens 4. In FIG. 3, the inspection target optical member 9 is moved in the right and left direction by means of the slide table unit 7.

The inspection target optical member 9 is placed such that the surface thereof facing the imaging lens 4 becomes conjugate with the imaging plane of the line sensor 5 with respect to the imaging lens 4. Thus, the line sensor 5 can form an image (one line) of a part of the surface of the inspection target optical member 9, and this part comprises the image inspection region thereof.

In FIG. 3, the image inspection region, which can be imaged onto the one line by the line sensor 5, is shown by a chain double-dashed line. In fact, the magnification of the imaging lens 4 (i.e., the position of the image pick-up device 3 itself, and the position of the imaging lens 4 with respect to the line sensor 5) is adjusted such that the image of the image inspection region of the inspection target optical member 9 is formed on the imaging plane of the line sensor 5 over the entire width thereof (i.e., the width in the pixel row direction of the line sensor 5).

The illumination lamp 1, in the form of an incandescent lamp, emits illumination light (white light), and is fixed to a frame, not shown, of the inspection apparatus.

The diffusion plate 2 is interposed between the illumination lamp 1 and the inspection target optical member 9. Further, as shown in FIG. 3, the diffusion plate 2 has a rectangular shape wider than the shorter side of the inspection target optical member 9, and has a rough surface that has been subjected to a coarsening process. Thus, the diffusion plate 2 receives the illumination light emitted from the illumination lamp 1 on its rear surface and transmits the illumination light therethrough while diffusing the same. The diffusion plate 2 crosses the optical axis l of the imaging lens 4 at a right angle and at the center thereof, and is fixed to a frame (not shown) of the inspection apparatus such that an outer edge thereof is parallel with the pixel row of the line sensor 5.

A strip-like light shielding plate 8 is stuck onto the surface of the diffusion plate 2. Further, the light shielding plate 8 is arranged in a direction parallel with the pixel row of the line sensor 5 and hence perpendicular to the optical axis l of the imaging lens 4. The center of the light shielding plate 8 coincides with the optical axis l of the imaging lens 4. The overall length of the light shielding plate 8 is longer than the shorter side of the inspection target optical member 9.

As shown in FIG. 3, when viewed from the position of the image pick-up device 3, the opposite ends of the light shielding plate 8 extend beyond the outer edge of the inspection target optical member 9. Moreover, as shown in FIG. 1, the width of the light shielding plate 8 is arranged to be greater than a spacing between marginal ray lines m,m of light that can be incident upon each pixel of the line sensor 5 in the absence of the inspection target optical member. Thus, the light shielding plate 8 shields the overall light which may be incident upon each pixel of the line sensor 5 so that with a perfect inspection target optical member 9 a dark background image is formed by the line sensor 5.

As shown in FIGS. 2 and 3, auxiliary illumination units 10, 10 are respectively disposed at opposite ends of the light shielding plate 8 in the longitudinal direction thereof. The auxiliary illumination units 10 each comprise an optical fiber bundle 11, a divergence restricting frame 12 which is provided at the emission end of the optical fiber bundle 11, and a collimator lens 13 which is disposed at the emission end of the divergence restricting frame 12. The divergence restricting frame 12 is a member which restricts the spreading of light from the emission end of the optical fiber bundle 11, which depends upon a predetermined numerical aperture, to only a direction along with the longitudinal direction of the light shielding plate 8. The collimator lens 13 is a lens for making parallel light rays which spread over a predetermined width (i.e., the width of the inspection target optical member×$2^{-\frac{1}{2}}$) in the divergence restricting frame 12. Further, the optical axis of the collimator lens 13 intersects at an angle of 45° to the optical axis l of the imaging lens 4 at the intersection of the optical axis l of the imaging lens 4 with the inspection target optical member 9. Thus, auxiliary illumination light rays emitted from each auxiliary illumination unit 10 can illuminate a portion, the image of which is captured on the line sensor 5 in the surface of the inspection target optical member 9 over the entire region thereof at a uniform luminance and angle.

Principle of detecting an optical defect

The following is an explanation about the principle by which an optical defect of the inspection target optical member 9 can be detected in the optical member inspection apparatus constructed in the aforesaid manner.

The light receiving surface of the pixel row of the line sensor 5 is regarded as being a line having almost no width.

Figure 4:
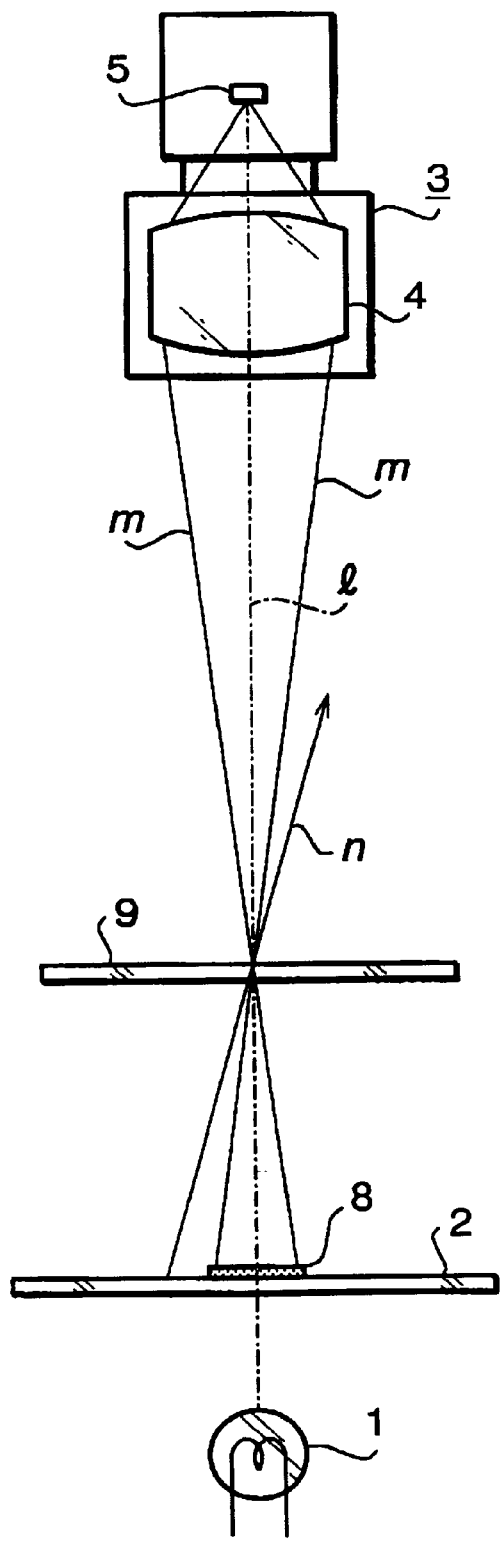
FIG. 4 is a front view showing light ray lines in the case where there is no optical defect in the optical member to be inspected.

With a perfect inspection target optical member, light which could be incident upon the imaging lens 4 and hence further incident upon each pixel of the line sensor 5 would be derived from principal ray(s) of light travelling along the optical axis l of the imaging lens 4 and which pass between the marginal ray lines m, m shown in FIG. 1. If these marginal ray lines m, m are extended in a reverse direction towards the light source, these marginal ray lines m, m intersect each other where the surface of the inspection target optical member is and then spread toward the diffusion plate 2. On the diffusion plate 2, these marginal rays m, m are shielded by the light shielding plate 8. Thus, as shown in FIG. 4, if there is no optical defect in the imaging inspection region of the inspection target optical member 9 (i.e., no defect in the region optically conjugate with the light receiving surface of the pixel row of the line sensor 5), light will in fact not be incident upon each pixel of the line sensor 5.

More specifically, a light ray n, which diffuses around the side of the light shielding plate 8 on the surface of the diffusion plate 2, is transmitted through the imaging region of the inspection target optical member 9, but passes outside the marginal ray lines m and m and, for this reason, the light ray n is not incident upon the imaging lens 4.

A light ray which diffuses around the side of the light shielding plate 8 on the surface of the diffusion plate 2 and which is transmitted through a portion other than the imaging region of the inspection target optical member 9, may be incident upon the imaging lens 4, but is not converged on each pixel of the line sensor 5. Therefore, image data output from the line sensor 5 represents an entire area of a dark image, except a bright portion (resulting from the diffuse light on the side) corresponding to the outer edge portion of the inspection target optical member 9.

Figure 5:
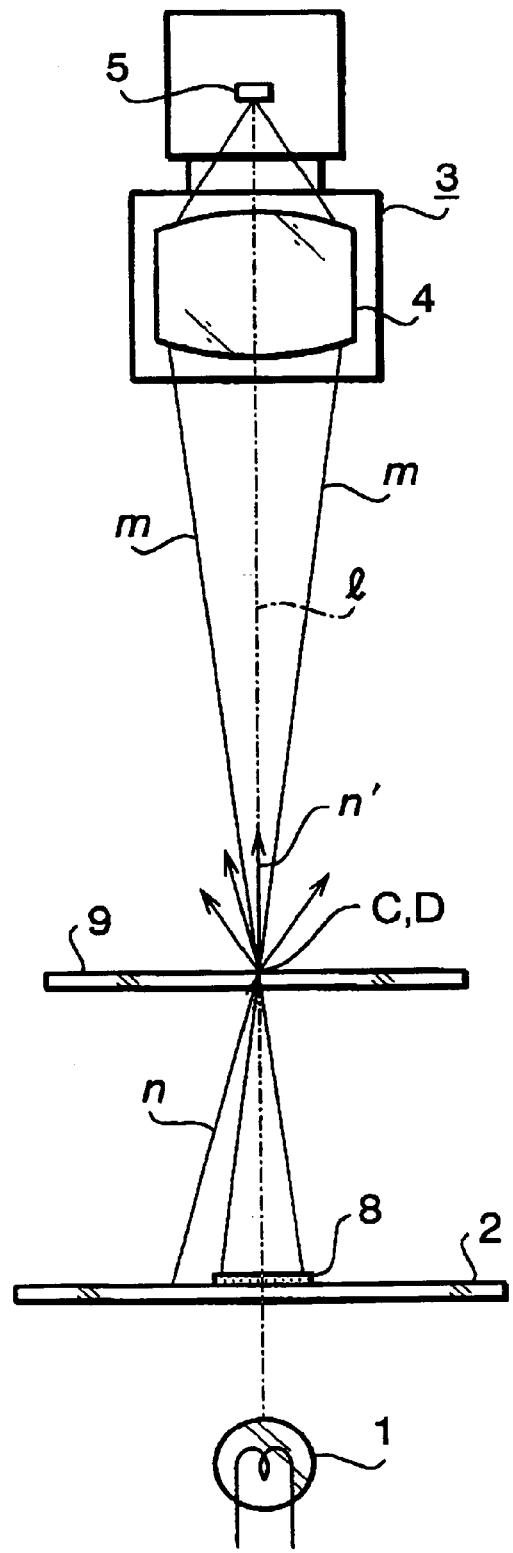
FIG. 5 is a front view showing light ray lines in the case where there is an optical defect in the optical member to be inspected.

On the contrary, as shown in FIG. 5, in the case where the inspection target optical member has a defect, in this case there is a scratch C and/or dust D in the imaging inspection region on the surface of the inspection target optical member 9, when a light ray n diffuses around the side of the light shielding plate 8 on the surface of the diffusion plate 2 and impinges on scratch C and/or dust D, the light n is diffused by scratch C and/or dust D. In this case, a diffused light ray n' can diverge at the point of intersection of the marginal ray lines m and m so that a part of that diffused light n' can be incident upon each pixel of the line sensor 5 via the imaging lens 4.

Figure 6:
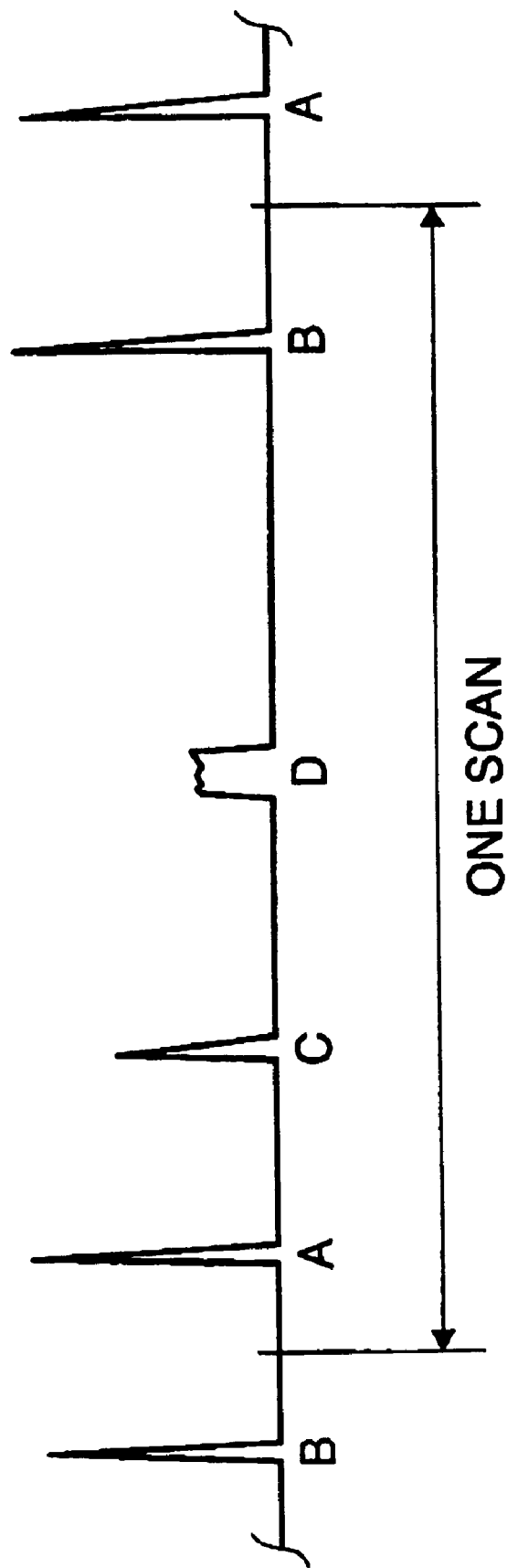
FIG. 6 is a graph showing a luminance distribution of image data outputted from a line sensor in the case where there is an optical defect in the optical member to be inspected.

Thus, an image of scratch C and/or dust D (i.e., an image brighter than a periphery) is formed on the imaging surface of the line sensor 5. Also, the aforesaid same diffusion is caused at outer edges A and B (see FIG. 3) of the inspection target optical member 9. For this reason, an image (i.e., an image brighter than a periphery) of these outer edges A and B is formed on the imaging surface of the line sensor 5. FIG. 6 is a graph showing a luminance distribution of the image data output from the line sensor 5 when imaging is carried out in the position shown in FIG. 1. FIG. 6 shows results based on the electric charge stored in each pixel by one-time imaging which is successively read by self-scan within a cycle of one scan.

Figure 7:
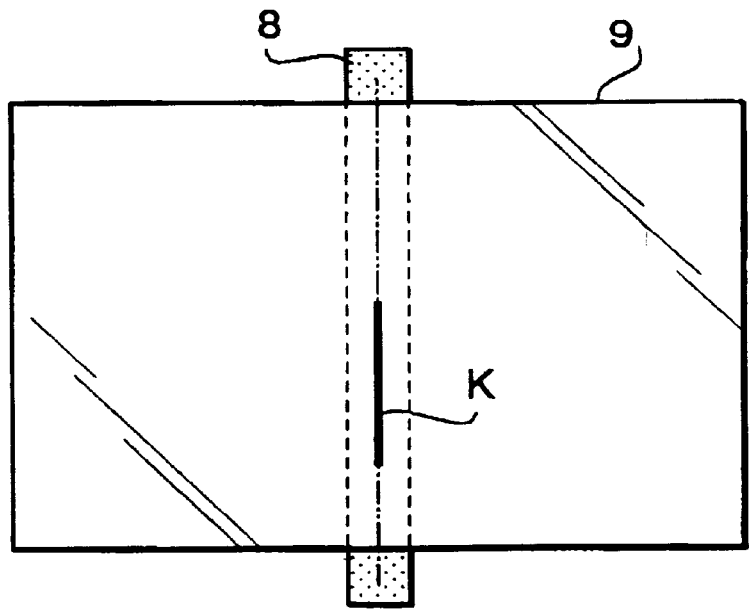
FIG. 7 is a plan view showing a state that a scratch or crack is formed in parallel with a longitudinal direction of a light shielding plate.
Figure 8:
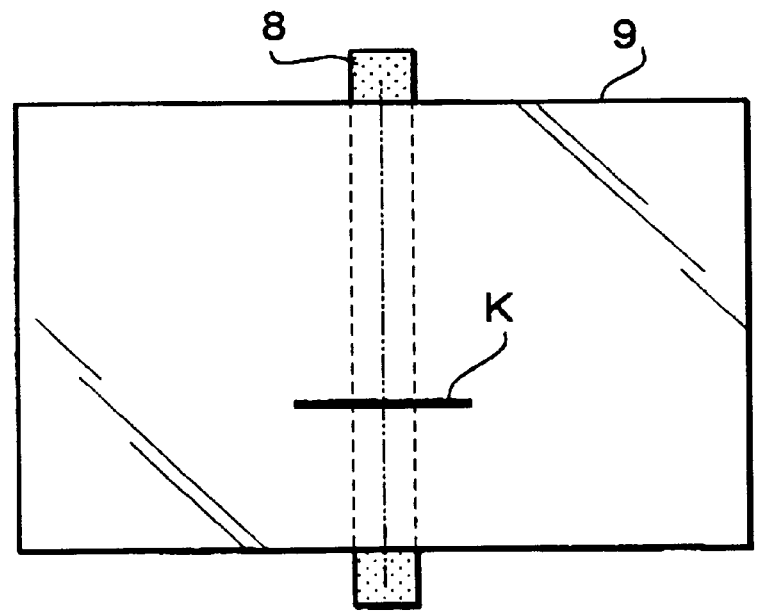
FIG. 8 is a plan view showing a state that a scratch or crack is formed perpendicularly to the longitudinal direction of the light shielding plate.
Figure 9:
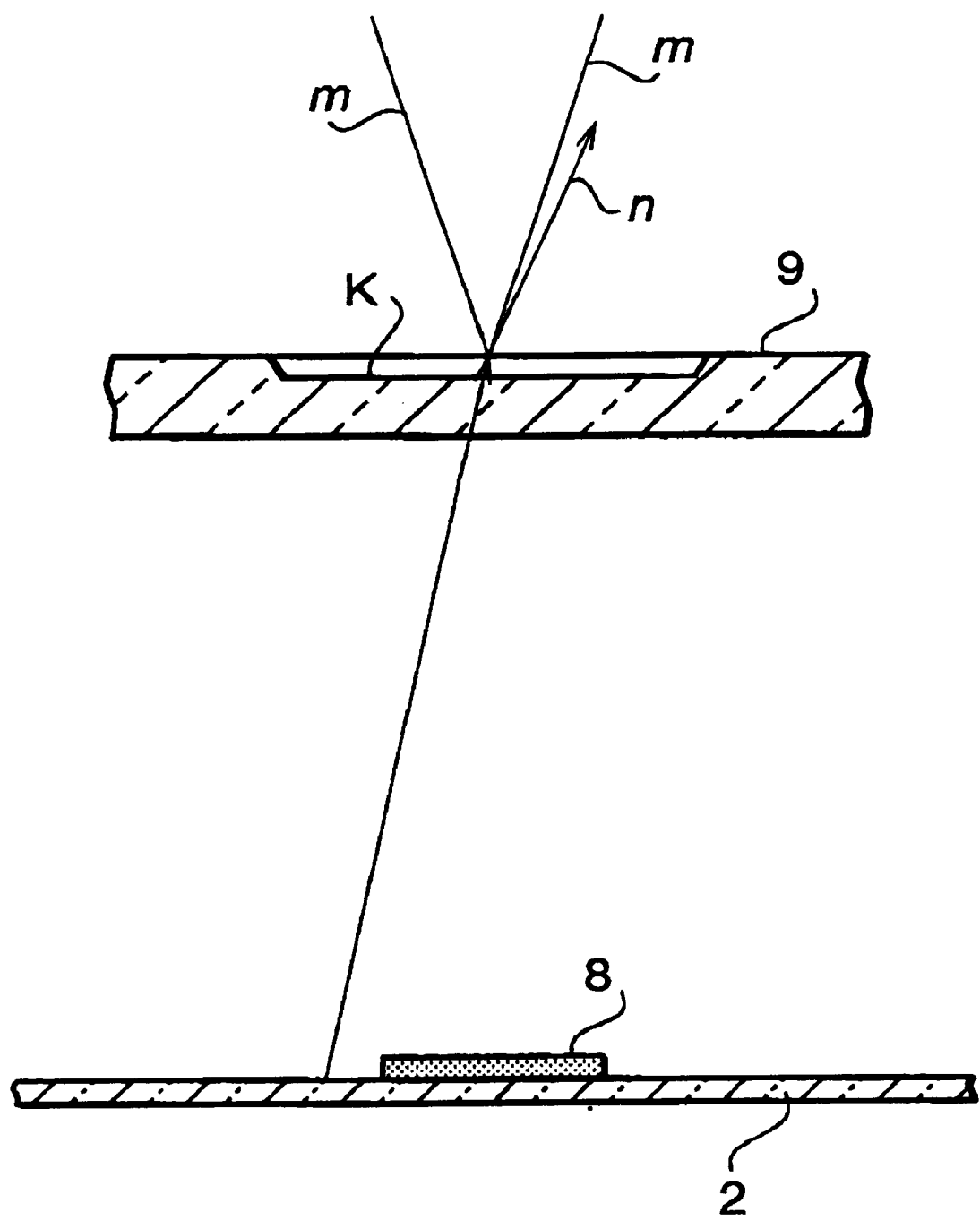
FIG. 9 is a sectional front view showing a state where an illuminating light transmits through the scratch or crack shown in FIG. 8.

A scratch or crack has such a tendency that light incident from a direction parallel to the direction of the scratch or crack will transmit therethrough without being diffused, while light incident from a direction perpendicular to the direction of the scratch or crack will be diffused therein. Thus, as shown in FIG. 7, in the case where a scratch or crack K is formed parallel to the longitudinal direction of the light shielding plate 8, a light ray n, which diffuses around the side of the light shielding plate 8 on the surface of the diffusion plate 2, is incident so as to be perpendicular to the scratch or crack K. For this reason, diffusion caused in the aforesaid manner will lead to a part of the diffused light being incident upon the imaging lens 4, and thus, an image of the scratch or crack K will be obtained by means of the line sensor 5. However, as shown in FIG. 8, in the case where a scratch or crack K is formed in a direction perpendicular to the longitudinal direction of the light shielding plate 8, as seen from FIG. 9 which is a longitudinally sectional view, a light ray n which diffuses around the side of the light shielding plate 8 on the surface of the diffusion plate 2, is incident parallel to the scratch or crack K. For this reason, the incident light ray n transmits therethrough without being diffused so that the light ray n travels outside the marginal ray lines m and m. Accordingly, the incident light ray n is not incident upon the imaging lens 4. Therefore, an image of the scratch or crack K is not obtained by means of the line sensor 5.

Figure 10:
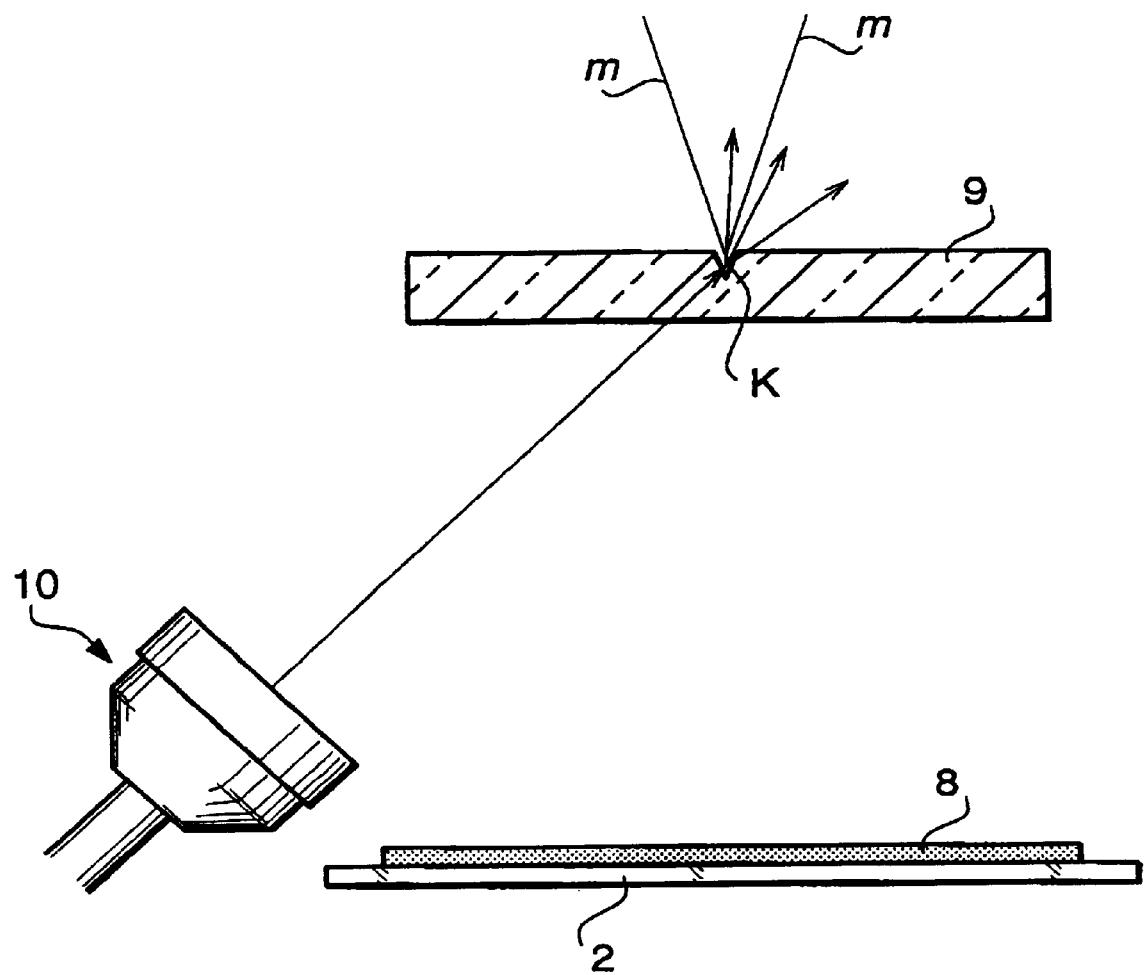
FIG. 10 is a sectional side view showing a state where an illuminating light from an auxiliary illuminating unit is diffused by the scratch or crack shown in FIG. 8.

In order to solve the aforesaid problem, in the present embodiment, the auxiliary illumination units 10 and 10 are provided. The auxiliary illumination unit 10 illuminates the image inspection region on the surface of the inspection target optical member 9 from a side in the longitudinal direction of the light shielding plate 8. Thus, as shown in FIG. 10, even in the case where a scratch or crack K is formed along a direction perpendicular to the longitudinal direction of the light shielding plate 8, the auxiliary illumination unit 10 can irradiate an illumination light into the scratch or crack K from a direction perpendicular thereto. As a result as shown in FIG. 10, a part of the diffused light is incident upon the imaging lens 4 so that an image of the scratch or crack K can be obtained by means of the line sensor 5.

Method of discriminating an optical defect

As described above, the imaging (charge storage and scan) by the line sensor 5 is carried out every time the inspection target optical member 9 is moved by a unit distance, in synchronism with the movement of the inspection target optical member 9 by the slide table unit 7. Then, every time the image capturing (charge storage and scan) by the line sensor 5 is carried out, the image data as shown in FIG. 6 is inputted to the image processor unit 6, and is written in the image memory 6a. FIG. 11A to FIG. 11D show a relationship between the light shielding plate 8, the imaging inspection region (shown by a chain double dotted line) by the line sensor 5 and the inspection target optical member 9, and the image data written in the image memory 6a. As shown in FIG. 11A to FIG. 11D, when the inspection target optical member 9 gradually passes through the imaging region (shown by a chain double dotted line) from a state shown in FIG. 11A toward a state shown in FIG. 11D, image data from the line sensor 5 for each scan is written in each line of the image memory 6a sequentially from the head line thereof.

In the present embodiment, after the image capturing by the line sensor 5 has fully completed, the image processor unit 6 makes a decision on the basis of the image data (FIG. 11D) stored in the image memory 6a corresponding to the entire surface of the inspection target optical member 9. Specifically, the image processor unit 6 compares a luminance of each pixel of the image data stored in the image memory 6a with a predetermined threshold value, and then executes a binarization process of setting a value of the pixel brighter than the predetermined threshold value as "1" while setting the value of pixels other than the above as "0". Subsequently, after the binarization process, if the sum total of the pixels having the value "1" exceeds a predetermined discrimination reference value, a decision is made that the inspection target optical member 9 is defective.

Control process

Figure 11A:
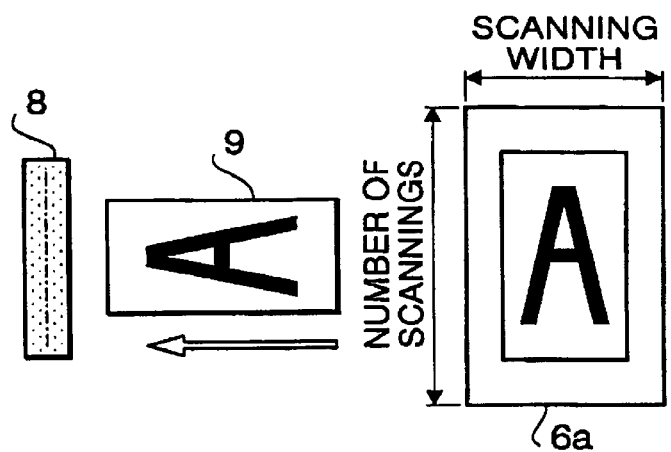
FIG. 11A to FIG. 11D are each a view showing a relationship between relative positions of the light shielding plate, an imaging region and the inspection target optical member, and an image data written in an image memory.
Figure 11B:
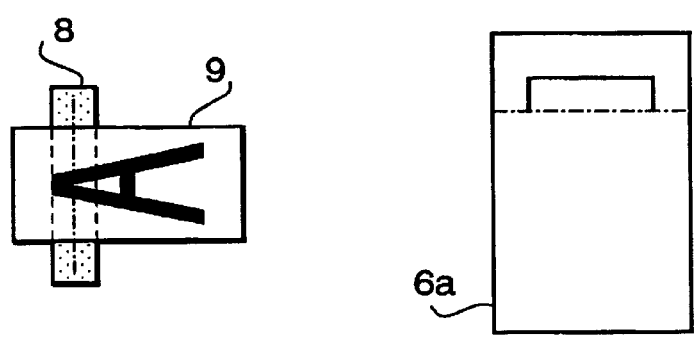
Figure 11C:
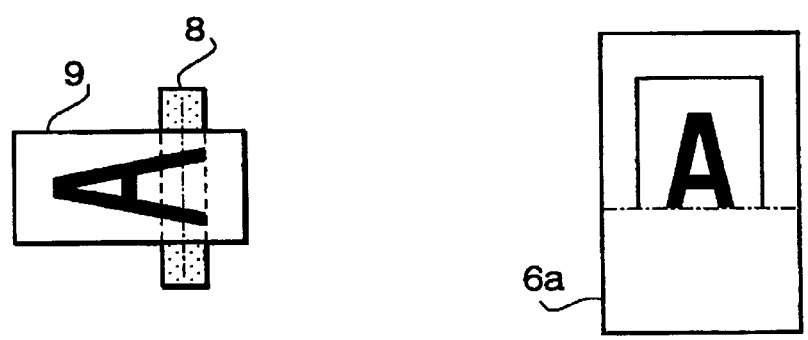
Figure 11D:
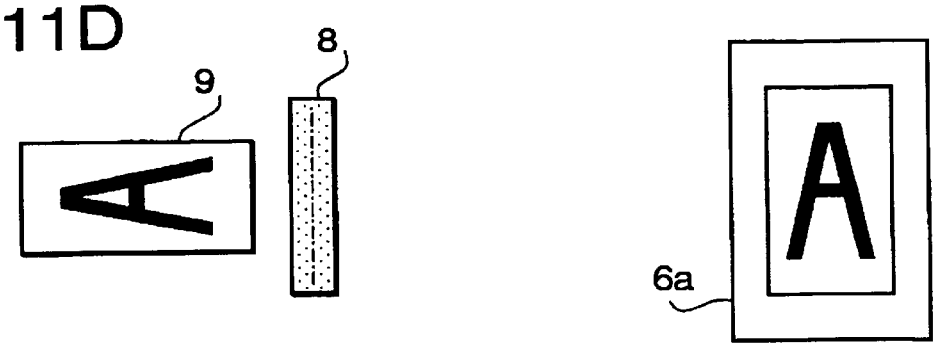

Next, in order to make a decision whether the inspection target optical member 9 is non-defective or defective, a control process is executed by the image processor unit 6. This will be explained below with reference to a flowchart shown in FIG. 12. Prior to the control process start, the following operating condition is set up. Specifically, the slider 7b of the slide table unit 7 is situated on the most right side end of the slide rail 7a shown in FIG. 1, and the inspection target optical member 9 is situated at a position spaced from the optical axis 1 of the imaging lens 4 as shown in FIG. 11A.

Figure 12:
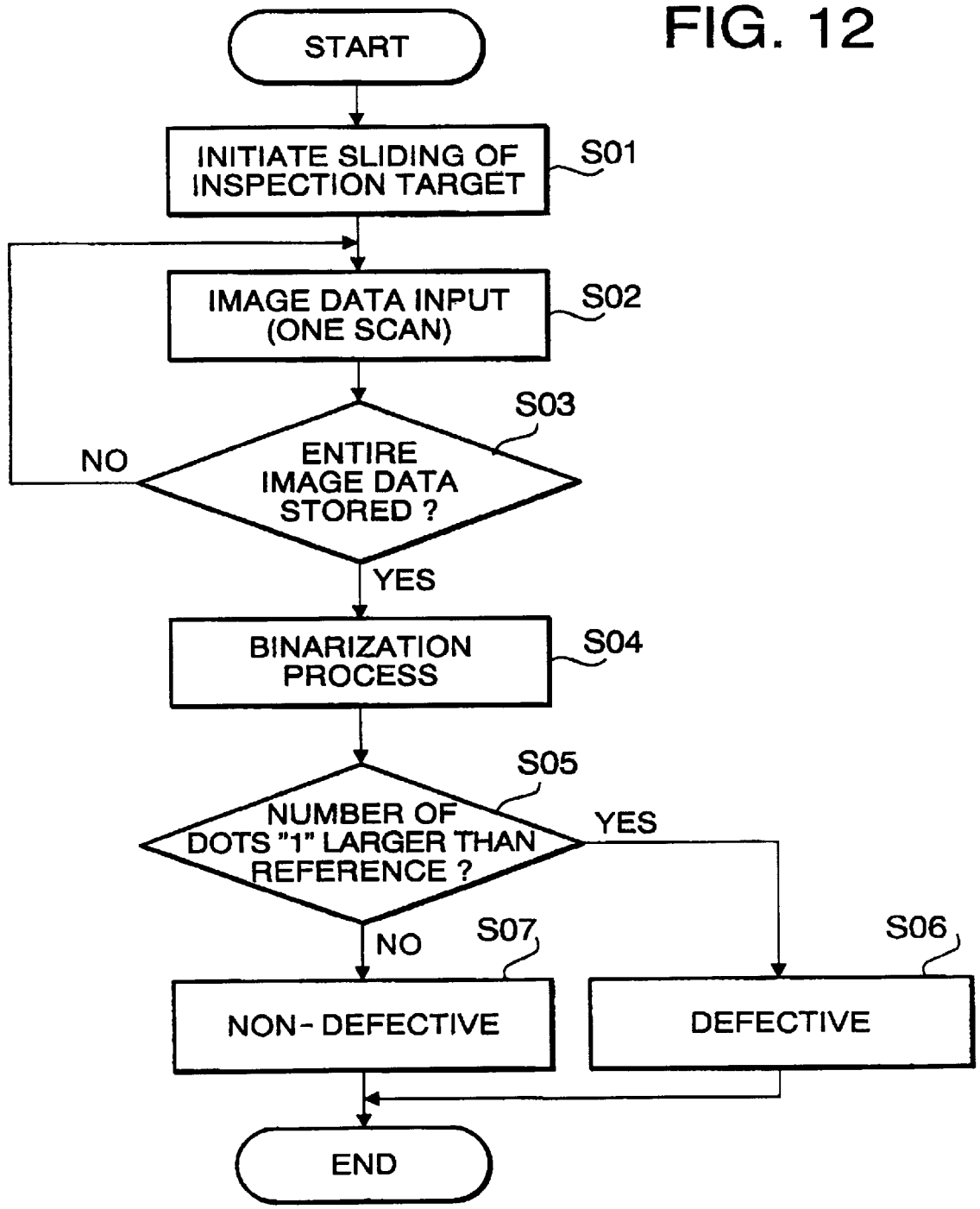
FIG. 12 is a flowchart showing the content of a control process carried out in the image processing unit shown in FIG. 1.

The control process of FIG. 12 is started by depressing an inspection start button (not shown) connected to the image processor unit 6. After the start, in the first step S01, the image processor unit 6 starts to output a drive signal to the driving motor 7e of the slide table unit 7 so that the inspection target optical member 9 is moved at a fixed speed.

Next, in step S02, the image processor unit 6 inputs an image data equivalent to one scan output from the line sensor 5, and writes it in the image memory 6a thereof.

Subsequently, in step S03, the image processor unit 6 makes a check whether an image data corresponding to the entirety of the inspection target optical member 9 has been stored in the image memory 6a according to the image data written in step S02. In the case where the image data corresponding to the entirety of the inspection target optical member 9 has still not been stored, the procedure is returned to step S02. Then, the image processor unit 6 again inputs an image data output from the line sensor 5 for next imaging.

In the case where the image data corresponding to the entirety of the inspection target optical member 9 has been stored, the inspection target optical member 9 is stopped from slidig, and then in step S04, the image processor unit 6 carries out a binarization process with respect to the image data written in the image memory 6a corresponding to the entirety of the inspection target optical member 9. More specifically, the image processor unit 6 compares a luminance of the overall pixels of the image data stored in the image memory 6a with a predetermined threshold value, and the value of the pixel having a luminance higher than the predetermined threshold value is substituted for "1" while the value of the pixel having a luminance lower than the predetermined threshold value is substituted for "0".

In the next step S05, the image processor unit 6 counts the sum total of pixels having the value "1" in the image memory 6a, and then, makes a check whether the number of pixels having the value "1" exceeds a predetermined discrimination reference value. If the number of pixels having the value "1" exceeds the predetermined discrimination reference value, then in step S06 a decision is made that the inspection target optical member 9 is defective, and the result is outputted by means of an image display, sound output, etc. If the number of pixels having the value "1" is less than the predetermined discrimination reference value, then in step S06 a decision is made that the inspection target optical member 9 is non-defective, and the result is outputted by means of an image display, sound output, etc. Thereafter, the image processor unit 6 ends the control process.

In place of the decision made in the above step S05, a decision may be made as to whether a diameter of a region consisting of a set of pixels having the value "1" is more than a predetermined value. Moreover, a decision may be made whether the sum total of the luminance value of an image is more than a predetermined value, but before the binarization of the region in the manner described above.

Operation of first embodiment

With the first embodiment thus constructed, light can be transmitted through the inspection target optical member 9, be incident upon the imaging lens 4, and be incident upon the pixel row of the line sensor 5. However, this light is normally shielded on the diffusion plate 2 by means of the light shielding plate 8. Therefore, if any optical defects in the inspection target optical member 9 are not within the imaging inspection region of the line sensor 5, dark image data from the line sensor 5 is produced as a whole.

If instead an optical defect in the inspection target optical member 9 is within the imaging inspection region by the line sensor 5, the light incident upon the region by passing around the side of the light shielding plate 8 is diffused by the optical defect, and then, a part of the diffused light is incident upon the imaging lens 4. As a result, the image data from the line sensor 5 shows a bright image of the optical defect which emphatically appears in a dark background.

Further, in the first embodiment, as a line sensor is employed for capturing an image, it is possible to improve a resolution (the sum total of pixels arranged in the pixel row direction) without making large the entirety of the sensor comparing to the case where an area sensor is employed. In addition, unlike the case of an area sensor, even if the number of pixels is increased to enhance the resolution, the width of the line sensor (i.e., a width in a direction perpendicular to the pixel row) is unchanged. Therefore, it is possible to make small the incident angle of light which is incident upon the imaging region in the inspection target optical member 9 passing around the side of the light shielding plate 8. As a result, even if the degree of diffusion is slight, the diffused light is still incident upon the imaging lens 4. That is, it is possible to make the detection sensitivity of optical defects higher than the case of the area sensor.

In summary, the number of pixels having a luminance higher than the predetermined discrimination reference value in the image data from the line sensor 5 is measured, and then the number of measured pixels is compared with the predetermined discrimination reference value. According to the comparative result, a decision is objectively made whether the inspection target optical member is non-defective or defective.

Modification of Embodiment 1

Figure 13:
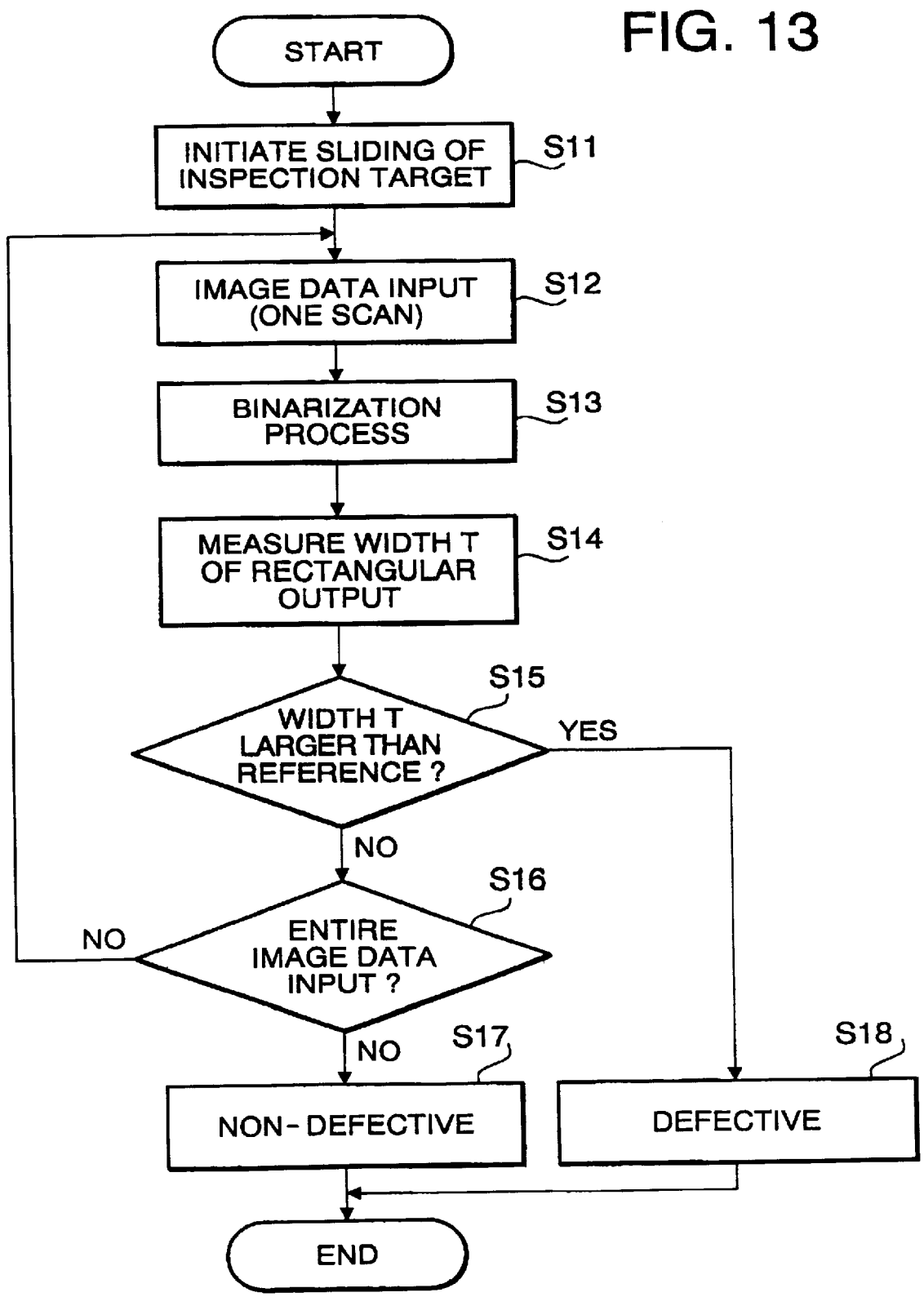
FIG. 13 is a flowchart showing the content of a control process carried out in the image processing unit in a modification of the first embodiment of the present invention.

This modification differs from the first embodiment in that the image processor unit 6 has no image memory 6a and the control process executed by the image processor unit 6 is shown in the flowchart of FIG. 13. In the control process according to the flowchart of FIG. 13, the binarization process and discrimination process is carried out directly with respect to image data for each line output from the line sensor 5.

The control process according to the flowchart of FIG. 13 is started by depressing an inspection start button (not shown) connected to the image processor unit 6. The same initial operating condition as in FIG. 12 is set up. After the start, in the first step S1, the image processor unit 6 starts to output a drive signal to the driving motor 7e of the slide table unit 7 so that the inspection target optical member 9 is moved at a fixed speed.

Next, the image processor unit 6 executes a loop process in steps S12 to S16. In the first step S12 in this loop process, the image processor unit 6 inputs an image data equivalent to one scan outputted from the line sensor 5.

In the next step S13, the image processor unit 6 executes a binarization process with respect to the image data equivalent to one scan inputted in the step S12. Specifically, the image processor unit 6 compares a luminance of the image data equivalent to one scan with a predetermined threshold value, and sets a portion (image data) having a luminance higher than the predetermined threshold value as a logic value "1" while setting a portion (image data) having a luminance equal to or lower than the predetermined threshold value as a logic value "0". By doing so, the image data is converted into a rectangular wave output.

In the next step S14, the image processor unit 6 measures a width T (i.e., a length of the portion of logic value "1") of the rectangular output converted in step S13.

In the next step S15, the image processor unit 6 makes a check whether or not the width T measured in step S14 is larger than a predetermined discrimination reference value. If the width T measured in step S14 is less than the predetermined discrimination reference value, the image processor unit 6 executes a procedure of step S16.

In this step S16, the image processor unit 6 makes a check whether the image data corresponding to the entirety of the inspection target optical member 9 has been completely inputted. If the image data corresponding to the entirety of the inspection target optical member 9 has still not been completely inputted, the image processor unit 6 returns the procedure to step S12 and then inputs an image data output from the line sensor 5 for next imaging.

The above loop process is repeated. If as a result, a decision is made in step S15 that the width T measured in step S14 exceeds the predetermined discrimination reference value, the image processor unit 6 makes a decision in step S18 that the inspection target optical member 9 is defective, and then outputs the result to an image display, sound output, etc. In this case, the input of image data after that is stopped, and at that point in time, the image processor unit 6 ends the control process.

If instead a decision is made in step S16 that the image data corresponding to the entirety of the inspection target optical member 9 has been completely input without braking a decision that the width T exceeds the predetermined discrimination reference value, then in step S17 the image processor unit 6 makes a decision that the inspection target optical member 9 is non-defective, and then outputs the result to an image display, sound output, etc. Thereafter, the processor unit 6 ends the control process.

The detailed construction of this modification is the same as the first embodiment, and the specific details thereof have been omitted for simplification.

Embodiment 2

A second embodiment of the present invention shows an optical member inspection apparatus which is suitable for inspecting an optical member such as a circular lens having a power around an optical axis.

It is not preferable to inspect such an optical member with the aforesaid construction of the first embodiment for the following reasons.

Figure 27A:
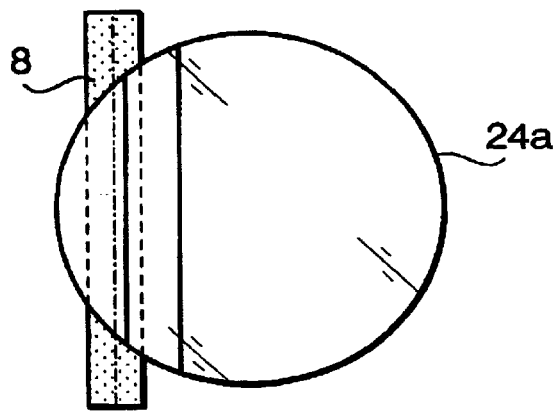
FIG. 27A to FIG. 27C are each an explanatory view showing a state of the light shielding plate observed in the case where a concave lens is inspected by means of the optical member inspection apparatus according to the first embodiment of the present invention.
Figure 27B:
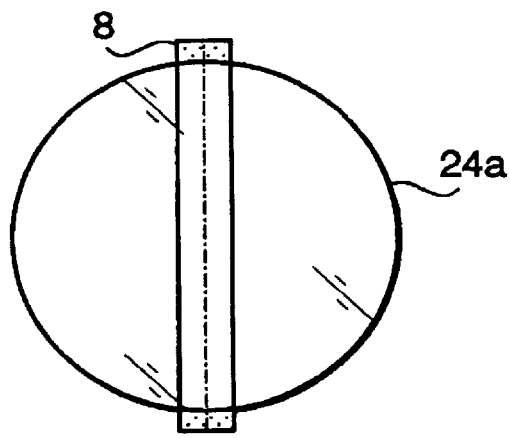
Figure 27C:
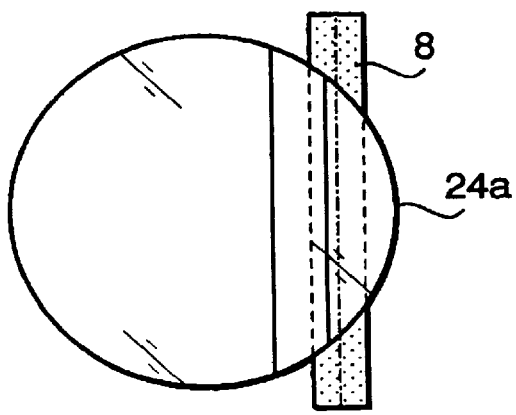

FIG. 27A to FIG. 27C each show a state viewed from the image pick-up device 3 when an optical member such as a concave lens 24a is attached to the slide table unit 7 of the first embodiment and is slidably moved thereon. As shown in FIG. 27A to FIG. 27C, when moving the concave lens 24a from the right-hand side toward the left-hand side in the figures with respect to the light shielding plate 8, the concave lens 24a and the light shielding plate 8 are observed in a state as shown in each of FIG. 27A to FIG. 27C.

Figure 28A:
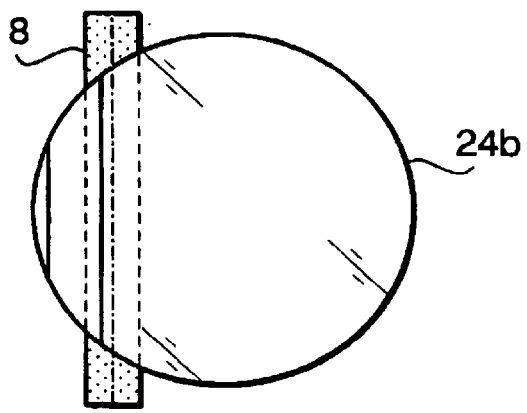
FIG. 28A to FIG. 28C are each an explanatory view showing a state of the light shielding plate observed in the case where a convex lens is inspected by means of the optical member inspection apparatus according to the first embodiment of the present invention.
Figure 28B:
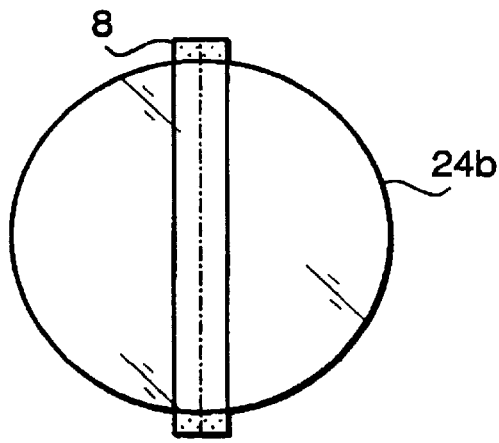
Figure 28C:
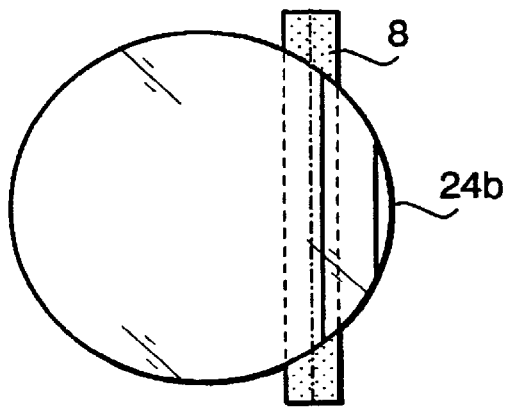

Likewise, FIG. 28A to FIG. 28C each show a state viewed from the image pick-up device 3 when an optical member such as a convex lens 24b is attached to the slide table unit 7 of the first embodiment and is slidably moved thereon. As shown in FIG. 28A to FIG. 28C, when moving the convex lens 24b from the right-hand side toward the left-hand side in the figure with respect to the light shielding plate 8, the convex lens 24b and the light shielding plate 8 are observed in a state as shown in each of FIG. 28A to FIG. 28C.

In the case where the optical axis of the respective inspection target optical members 24a or 24b is offset from the center of the light shielding plate 8, the light shielding plate B observed through these inspection target optical members 24a and 24b is observed in a state which appears shifted from the actual position, as represented by the solid vertical lines shown in FIGS. 27A and 27C and FIGS. 28A and 28C. As a result, even if these inspection target optical members 24a and 24b have no optical defect, light which diffuses around the side of the light shielding plate 8 on the diffusion plate 2 is incident upon the imaging lens 4. For this reason, image data obtained by the line sensor 5 becomes bright. Thus, the bright image derived from an optical defect is not so easily resolved and there is the possibility that a portion having no optical defect is regarded as being optically defect.

In view of the aforesaid circumstances, according to the second embodiment, in order to always make a coincidence of the optical axis of an inspection target optical member 24 with the center of the light shielding plate 8, the inspection target optical member 24 is rotated around the optical axis thereof.

Arrangement of the optical member inspection apparatus

Figure 14:
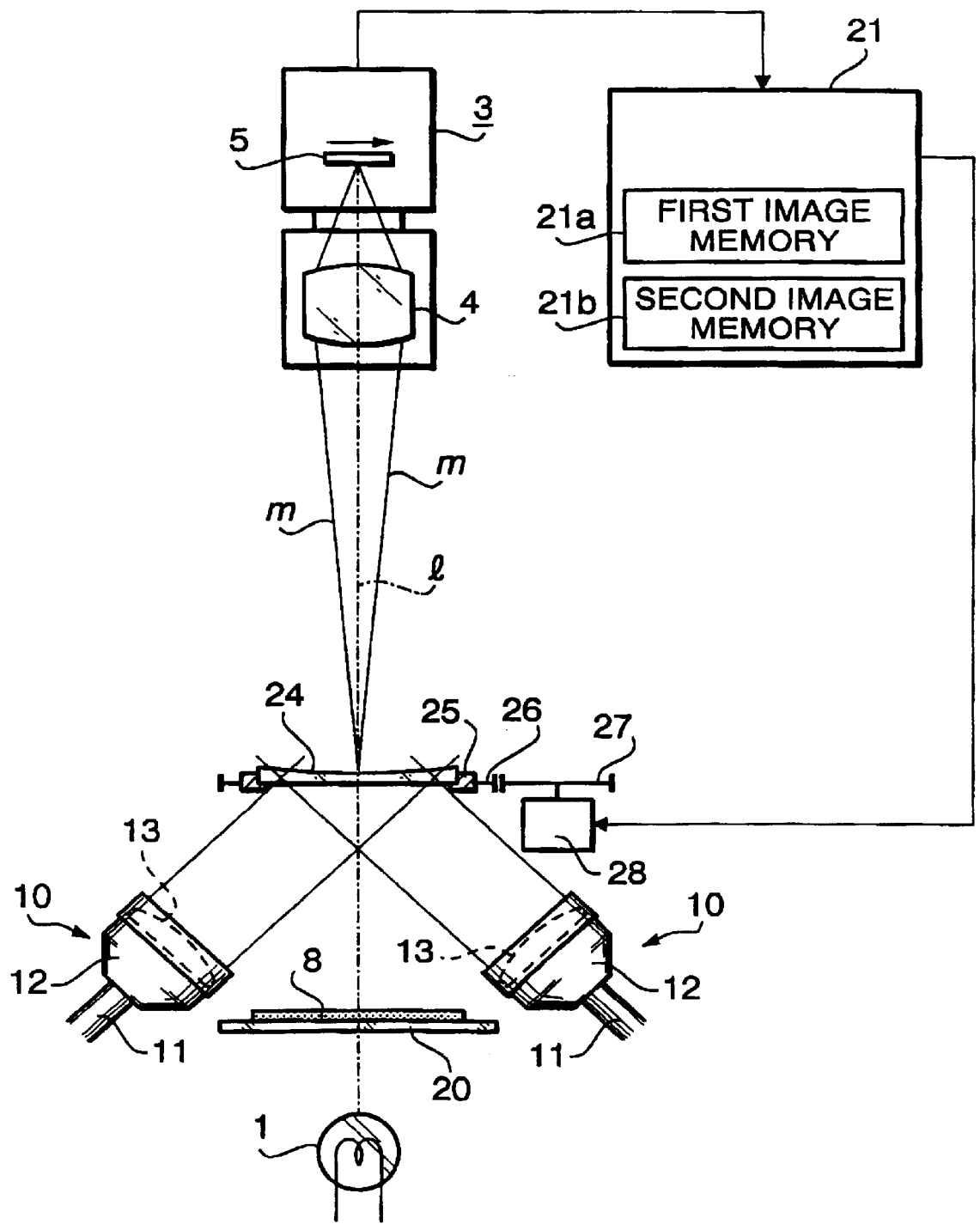
FIG. 14 is a side view schematically showing an optical member inspection apparatus according to a second embodiment of the present invention.

FIG. 14 is a side view schematically showing an optical member inspection apparatus according to the second embodiment of the present invention. Components common to the first embodiment bear common reference numerals.

As shown in FIG. 14, the optical member inspection apparatus comprises an illumination lamp 1, a diffusion plate 20, and an image pick-up device 3, which are arranged on the same optical axis l.

In this second embodiment, an image processor unit 21 outputs a control signal to a driving motor 28 for rotating the inspection target optical member 24 in synchronism with image data output from the line sensor 5. The image processor unit 21 has a built-in first image memory 21a and second image memory 21b for storing the image data.

The driving motor 28 is provided with a pinion gear 27. The pinion gear 27 engages with an annular gear 26 which is attached onto a peripheral edge of an annular holder 25 centered around the optical axis l of the imaging lens 4. The annular holder 25 holds the peripheral edge of the inspection target optical member 24, which is a circular lens, over the entire circumference thereof. Thus, so long as the center of the inspection target optical member 24 and the optical axis thereof coincides with each other, the optical axis of the inspection target optical member 24 is coaxial with the optical axis l of the imaging lens 4.

When the aforesaid control signal is output from the image processor unit 21, the driving motor 28 is rotated according to the control signal. Thus, the holder 25 is driven via both gears 27 and 26, and accordingly the inspection target optical member 24 held by the holder 25 is rotated at a fixed speed in a plane perpendicular to the optical axis l of the imaging lens 4. That is, the driving motor 28, two gears 27 and 26, and holder 25 constitute a rotating unit for rotating the inspection target optical member 24 around the optical axis l of the imaging lens 4.

In the present case, as shown in FIG. 15A, a rotating direction of the inspection target optical member 24 is a counterclockwise direction viewed from the image pick-up device 3. FIG. 15A is a plan view of the inspection target optical member 24 as viewed from the image pick-up device 3.

The diffusion plate 20 is interposed between the illumination lamp 1 and the inspection target optical member 24. Further, as shown in FIG. 15A, the diffusion plate 20 has a disc shape having a diameter larger than the inspection target optical member 24, and its surface is processed as a coarse surface. Thus, the diffusion plate 20 receives an illumination light emitted from the illumination lamp 1 on the overall rear face thereof, and diffuses the illumination light. Also, the diffusion plate 20 is fixed to a frame (not shown) of the optical member inspection apparatus so as to be perpendicular to the optical axis l of the imaging lens 4 in the center thereof.

Method of discriminating an optical defect

In this second embodiment, the imaging process (charge storage and scan) by the line sensor 5 is carried out every time the inspection target optical member 24 is rotated by only a unit angle, in synchronism with rotation of the inspection target optical member 24 by the driving motor 28. Then, every time the image pick-up by the line sensor 5 is carried out, image data as shown in FIG. 15B is inputted to the image processor unit 21, and is written in the first image memory 21a.

Figure 16A:
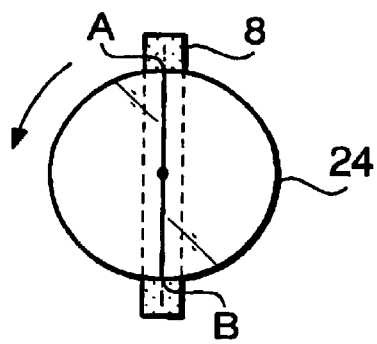
FIG. 16A and FIG. 17A are each a view showing a relationship between relative positions of the light shielding plate, an imaging region and the inspection target optical member, and image data written in a first image memory.
Figure 17A:
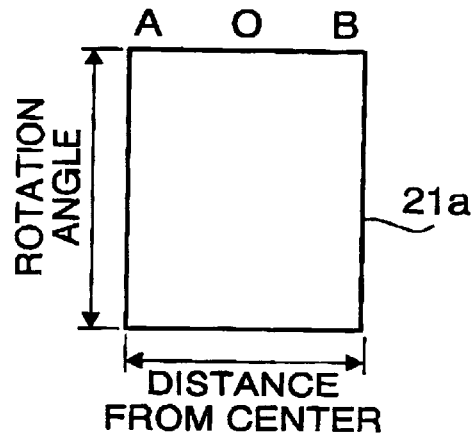
Figure 16B:
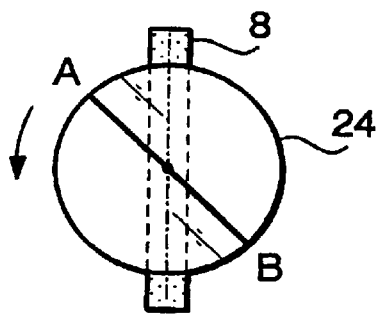
FIG. 16B and FIG. 17B are each a view showing a relationship between relative positions of the light shielding plate, an imaging region and the inspection target optical member, and image data written in the first image memory.
Figure 17B:
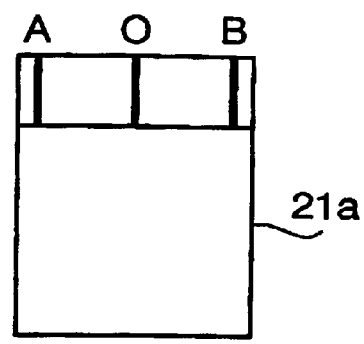

FIG. 16A to FIG. 16E and FIG. 17A to FIG. 17E show a relationship between relative positions of the light shielding plate 8, an imaging inspection region (shown by a chain double dotted line) of the line sensor 5 and the inspection target optical member 24, and the image data written in the first image memory 21a, respectively. More specifically, FIG. 16A and FIG. 17A show the initial state (image points on the peripheral edge of the inspection target optical member 24 at this point of time are respectively set as "A" and "B"). FIG. 16B and FIG. 17B show a state where the inspection target optical member 24 is rotated by an angle of 45° in the counterclockwise direction from the initial state.

Figure 16C:
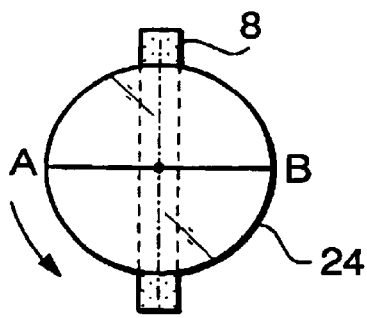
FIG. 16C and FIG. 17C are each a view showing a relationship between relative positions of the light shielding plate, an imaging region and the inspection target optical member, and image data written in the first image memory.
Figure 17C:
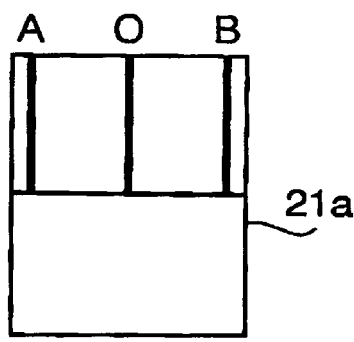
Figure 16D:
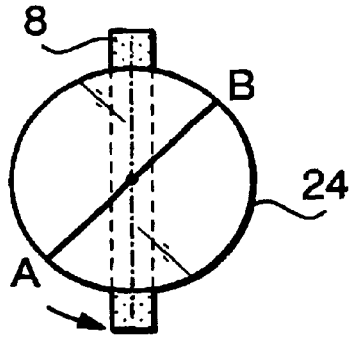
FIG. 16D and FIG. 17D are each a view showing a relationship between relative positions of the light shielding plate, an imaging region and the inspection target optical member, and image data written in the first image memory.
Figure 17D:
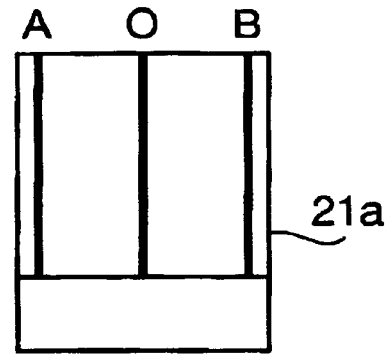
Figure 16E:
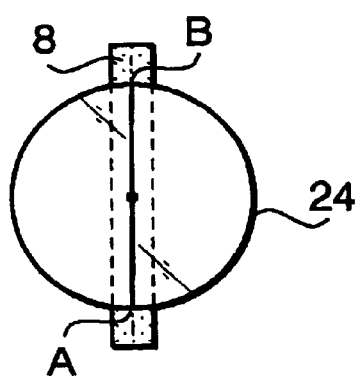
FIG. 16E and FIG. 17E are each a view showing a relationship between relative positions of the light shielding plate, an imaging region and the inspection target optical member, and image data written in the first image memory.
Figure 17E:
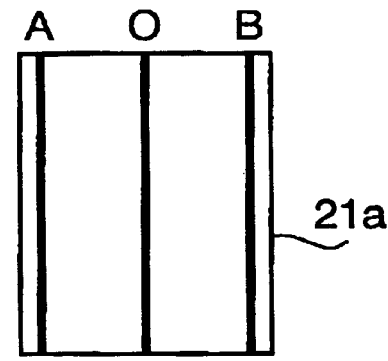

FIG. 16C and FIG. 17C show a state where the inspection target optical member 24 is rotated by an angle of 90° in the counterclockwise direction from the initial state. FIG. 16D and FIG. 17D show a state that the inspection target optical member 24 is rotated by an angle of 135° in the counterclockwise direction from the initial state. FIG. 16E and FIG. 17E show a state that the inspection target optical member 24 is rotated by an angle of 180° in the counterclockwise direction from the initial state. As shown in each of these figures, when the inspection target optical member 24 is gradually rotated, image data from the line sensor 5 for each scan is written in each line of the first image memory 21a sequentially from the head line thereof.

At the point of time as shown in FIG. 16E and FIG. 17E, an ordinate of the image data written in the first image memory 21a shows a rotation angle of the inspection target optical member 24 on the basis of a diameter connecting between points A and B. On the other hand, an abscissa of the image data shows a distance from the center (optical axis) O of the inspection target optical member 24 in the diameter direction thereof. That is, a coordinate system of the image data written in the first image memory 21a is a polar coordinate system. In the polar coordinate system, the nearer a defect is situated to the center O of the inspection target optical member 24, the greater the defect area is transferred therein. On the other hand, the nearer a defect is situated to the outer edges thereof, the smaller the defect area is transferred therein. For this reason, it is impossible to make a decision whether the inspection target optical member 24 is non-defective on the basis of only the image data written in the first image memory 22a. In view of the aforesaid circumstances, in this second embodiment, the image processor unit 21 converts the image data of the polar coordinate system written in the first image memory 21a into an image data of a rectangular coordinate system, and then, writes the converted image data in the second image memory 21b.

Figure 18:
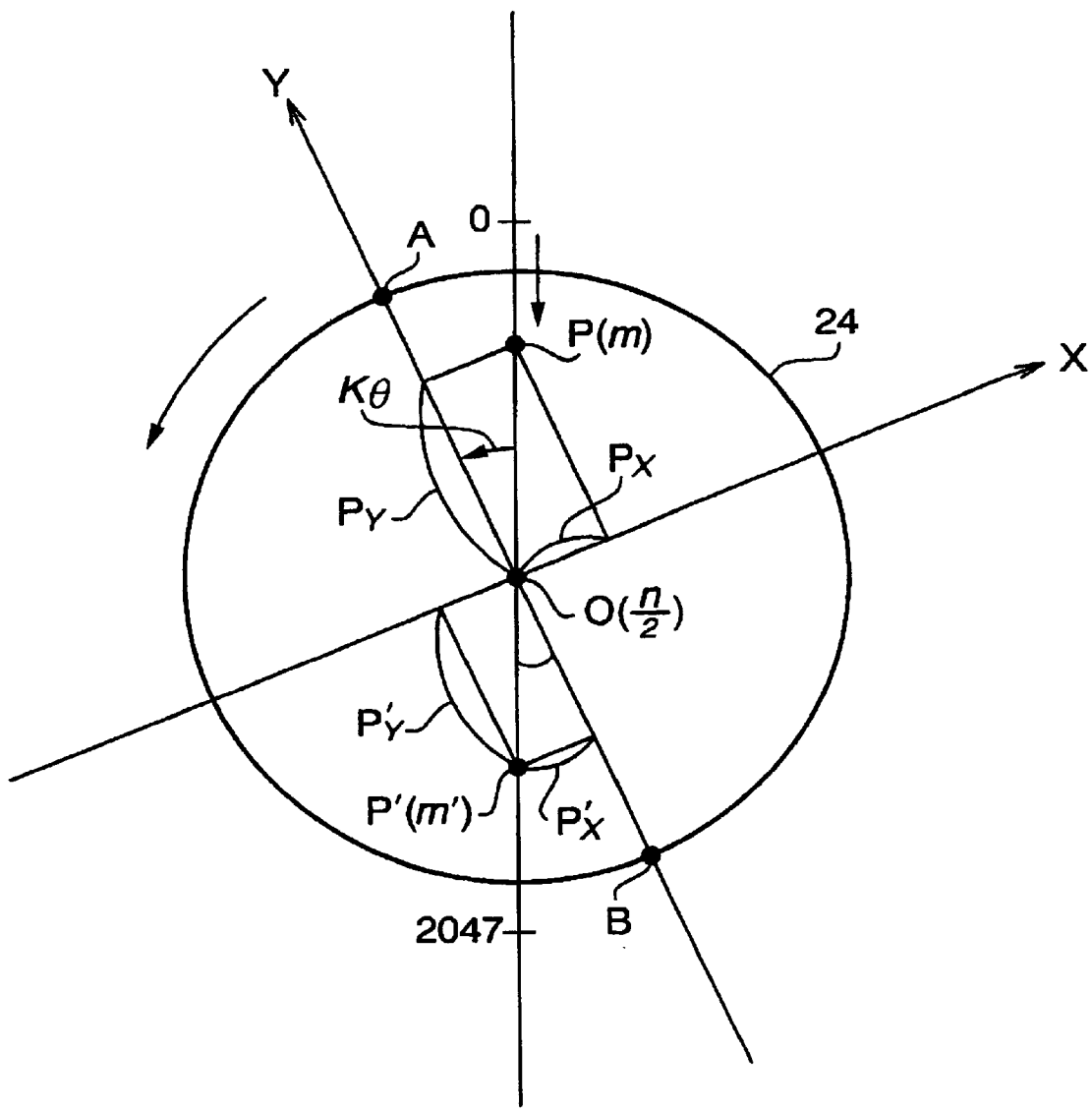
FIG. 18 is a view showing a coordinate transformation method from a polar coordinate system to a rectangular coordinate system.

FIG. 18 is a view showing a coordinate transformation method from the aforesaid polar coordinate system to the rectangular coordinate system. Further, FIG. 18 shows a relationship between a local coordinate system defined on the surface of the inspection target optical member 24 and an absolute coordinate system taking the pixel direction of the line sensor 5 as ordinate. In FIG. 18, the local coordinate system defined on the surface of the inspection target optical member 24 sets the optical axis O of the inspection target optical member 24 as the origin 0, and takes the line connecting points A and B on the outer edges of the inspection target optical member 24 as a Y-axis. Further, the local coordinate system takes the line which is perpendicular to the Y-axis and passes through the origin 0 as an X-axis. On the other hand, since a value of each point on the ordinate of the absolute coordinate system corresponds to a scan sequence of each pixel of the line sensor 5, assuming that the resolution (number of pixels) of the line sensor 5 is set as "n", a point "n" have a value of 0 to (n−1). At the point n/2, the ordinate of the absolute coordinate system intersects the origin 0 of the local coordinate system.

When the inspection target optical member 24 is rotated, the local coordinate system rotates around the origin 0 in the counterclockwise direction with respect to the ordinate of the absolute coordinate system. At this time, assuming that the number of times of image capturing from the start (number of times of scan) is set as "k", and a rotation angle of the inspection target optical member 24 for one cycle (one scan) of the image capturing is set as θ, the polar coordinate of the $m^{th}$ pixel P (where $0 \leq m \leq n/2$) of the line sensor 5 in the local coordinate system is the point P (n/2−m, kθ), whilst the polar coordinate of the m'$^{th}$ pixel P' (where n/2<m'≦(n−1)) of the line sensor 5 in the local coordinate system is the point P' (m−n/2, (π+kθ)).

If these polar coordinates P and P' are expressed on the rectangular coordinate system, the coordinates are P(Px, Py), P'(Px', Py'), where, these coordinates are expressed by the following equations:

$$Px = (n/2-m) \sin k\theta \quad (1)$$

$$Py = (n/2-m) \cos k\theta \quad (2)$$

$$Px' = (m'-n/2) \sin (\pi+k\theta) = -(m'-n/2) \sin k\theta \quad (3)$$

$$Py' = (m'-n/2) \cos (\pi+k\theta) = -(m'-n/2) \cos k\theta \quad (4)$$

Therefore, by making use of these equations (1) to (4), the polar coordinate system can be transferred into the rectangular coordinate system.

Figure 19B:
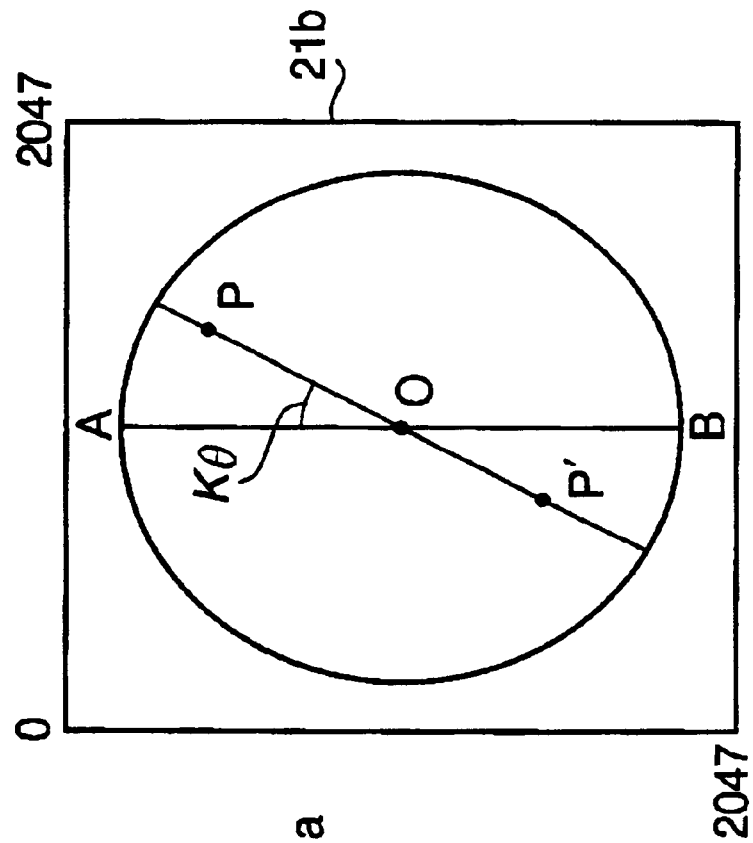
FIG. 19A and FIG. 19B are each a memory map showing image data stored in each image memory shown in FIG. 14.
Figure 19A:
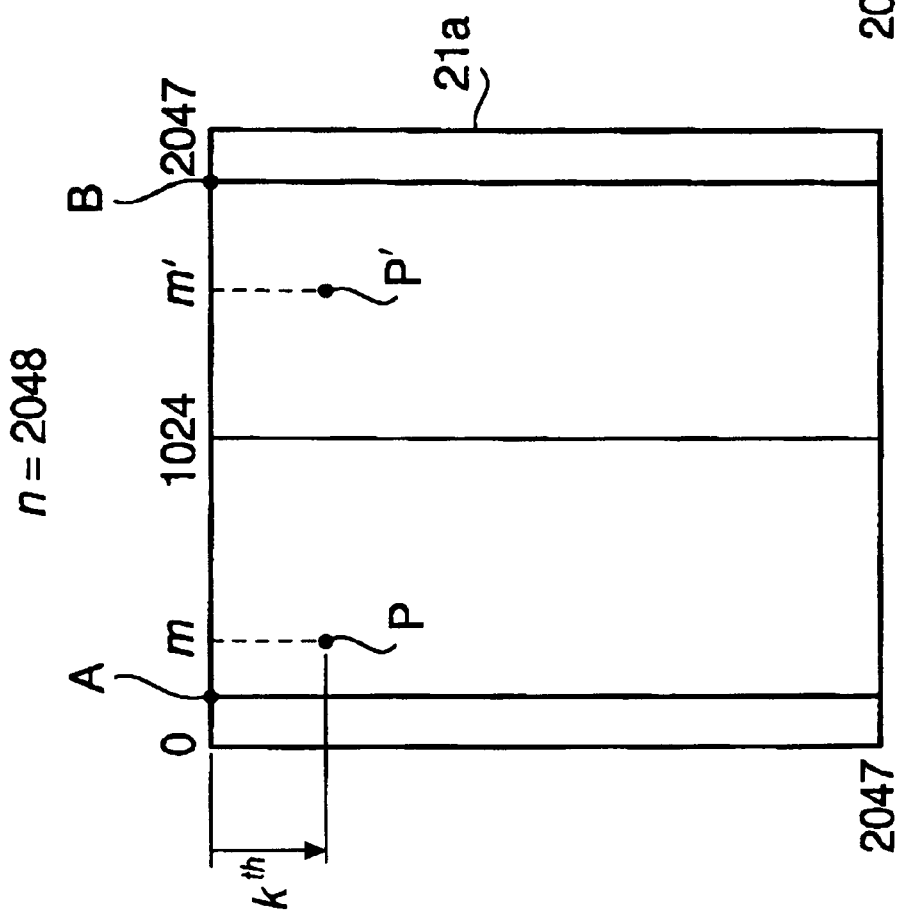

Now, as shown in FIG. 19A, the number of pixels n of the line sensor 5 (resolution) is 2048. In addition, 2048 imagings are carried out while the inspection target optical member 24 makes a half rotation of 180°, i.e., θ=180/2048. In this case, the image processor unit 21 applies the above equations (1) and (2) to the pixels from 0 to the 1024$^{th}$ columns of the first image memory 21a, and applies the above equations (3) and (4) to the pixels from 1025$^{th}$ to 2047$^{th}$ columns thereof. However, the origin (0, 0) of the second image memory 21b is situated at the upper left; for this reason, a correction needs to be made for shifting the position of origin. More specifically, the second image memory 21b has 2048×2048 pixels. For this reason, the image processor unit 21 must make a correction in a manner of evenly adding 1024 to an X coordinate value obtained from the above equations (1) and (3), and evenly adding 1024 to a Y coordinate value obtained from the above equations (2) and (4) after reversing the polarity of the Y coordinate value.

That is, the image processor unit 21 executes the following equations (1') and (2') with respect to the pixel of k$^{th}$ line and m$^{th}$ column (m=0 to 1024) of the first image memory 21a shown in FIG. 19A.

$$Px = 1024 + (1024-m) \sin k\theta \quad (1')$$

$$Py = 1024 - (1024-m) \cos k\theta \quad (2')$$

Based on the value Px and Py thus obtained, the pixel of Py$^{th}$ line and Px$^{th}$ column of the second image memory 21b shown in FIG. 19B is specified as a pixel after transformation. Then, the data written in the pixel of k$^{th}$ line and m$^{th}$ column of the first image memory 21a is written and transferred into the pixel of Py$^{th}$ line and Px$^{th}$ column of the second image memory 21b.

On the other hand, the image processor unit 21 executes the following equations (3') and (4') with respect to the pixel of k$^{th}$ line and m'$^{th}$ column (m'=1025 to 2047) of the first image memory 21a shown in FIG. 19A.

$$Px' = 1024 - (m'-1024) \sin k\theta \quad (3')$$

$$Py' = 1024 + (m'-1024) \cos k\theta \quad (4')$$

Based on the value Px' and Py' thus obtained, the pixel of Py'$^{th}$ line and Px'$^{th}$ column of the second image memory 21b shown in FIG. 19B is specified as a pixel after transformation. Then, the data written in the pixel of k$^{th}$ line and m$^{th}$ column of the first image memory 21a is written and transferred into the pixel of Px'$^{th}$ line and Py'$^{th}$ column of the second image memory 21b.

In the manner as described above, the image data is written and transferred, and then, the image data stored in the second image memory 21b is equivalent to an image data which is obtained by picking up the image of the inspection target optical member 24 with the use of an area sensor. Thus, an optical defect area of the image data has a proportional relationship to the actual optical defect area regardless of a position of the optical defect. The image processor unit 21 makes a decision whether the inspection target optical member 24 is non-defective or defective on the basis of the image data stored in the second image memory 21b. More specifically, the image processor unit 21 compares a luminance of each pixel of the image data stored in the second image memory 21b with a predetermined threshold value, and then executes a binarization process in a manner of setting a value of pixels having a luminance brighter than the predetermined threshold value as "1" while setting a value of pixels other than the above pixel "0". After the binarization process, if the sum total of pixels having the value "1" exceeds a discrimination reference value, the image processor unit 21 makes a decision that the inspection target optical member 24 is defective.

Control process

Next, in order to make a decision whether the inspection target optical member 24 is non-defective or defective, the content of a control process executed by the image processor unit 21 will be explained below with reference to a flowchart shown in FIG. 20.

Figure 20:
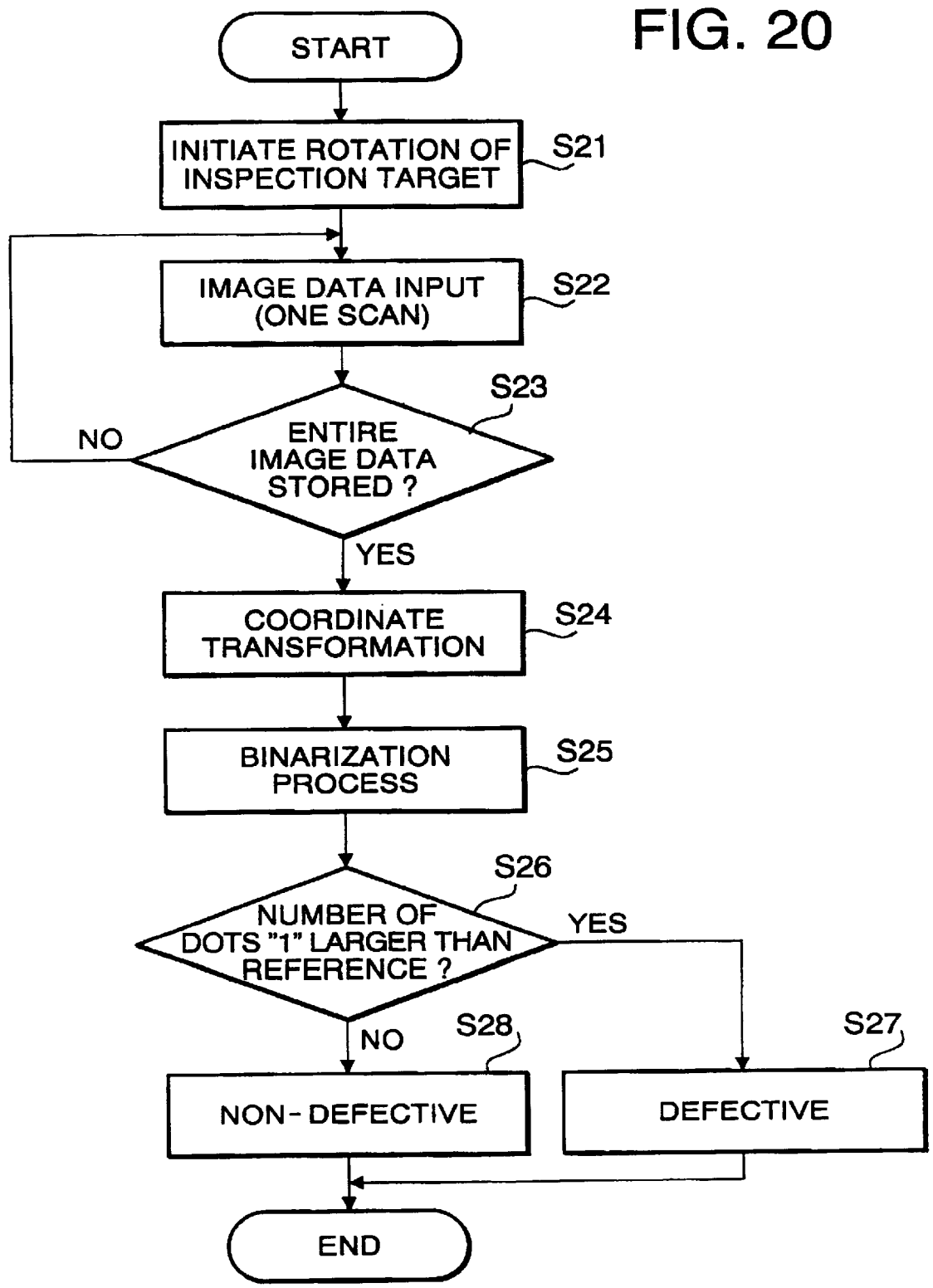
FIG. 20 is a flowchart showing the content of a control process carried out in the image processing unit shown in FIG. 14.

The control process of FIG. 20 is carried out in the same manner as the control process of FIG. 12, except for the following matters. Specifically, in the first step S21, after the start, a driving signal is outputted to the driving motor 28, and the inspection target optical member 24 is rotated at a fixed speed, and further, in step S24, a coordinate transformation is carried out with respect to the image data of the polar coordinate system written in the first image memory 21a with the use of the above equations (1') to (4'), and the image data transferred to the rectangular coordinate system is written in the second image memory 21b.

Operation of second embodiment

With the second embodiment thus constructed, a lens having a refractive power centered around the optical axis thereof can be used as the inspection target optical member 24, and the optical axis of the inspection target optical member 24 is made coincident with the optical axis l of the imaging lens 4. In addition, the inspection target optical member 24 is rotated around the optical axis l. Thus, when viewing from the position of the image pick-up device 3, even if the inspection target optical member is rotated, the light shielding plate 8, which is observed through the inspection target optical member 24, is unchanged in position around the optical axis of the inspection target optical member 24. Therefore, if the inspection target optical member 24 does not have an optical defect, a dark image of the inspection target optical member 24 is always obtained by the line sensor 5. However, if the inspection target optical member 24 has an optical defect, the obtained image data becomes bright in accordance with the degree of optical defect.

The data of the polar coordinate system is converted into the data of the rectangular coordinate system, and then, the number of pixels having a luminance higher than the predetermined discrimination reference value in the data of the rectangular coordinate system after transformation is measured. Further, the measured number of pixels is compared with the predetermined discrimination reference value, and then, in accordance with the comparative result, a decision is objectively made whether the inspection target optical member 24 is non-defective or defective.

Figure 22:
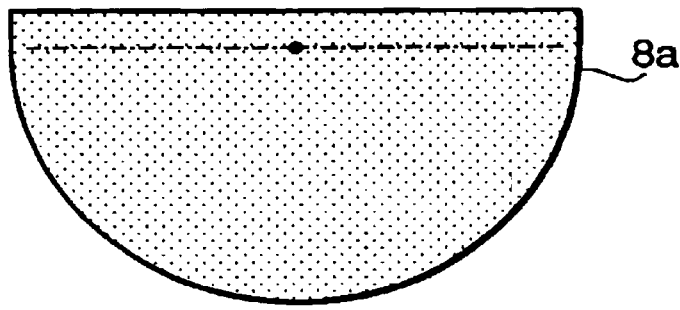
FIG. 22 is a plan view showing a modification of the light shielding plate.

The detection of an optical defect by use of the aforesaid diffused light is established even if a direction of a light incident upon the imaging inspection region of the inspection target optical member 24 is in only one direction. Thus, in place of the aforesaid light shielding plate 8, a light shielding plate 8a having a substantially semi-circular shape as shown in FIG. 22 may be used.

Figure 23:
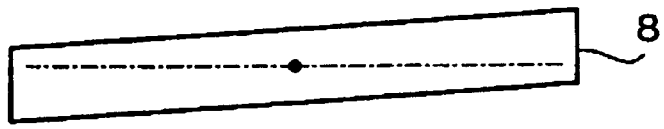
FIG. 23 is a plan view showing where the light shielding plate is observed in a state of being distorted.
Figure 24:
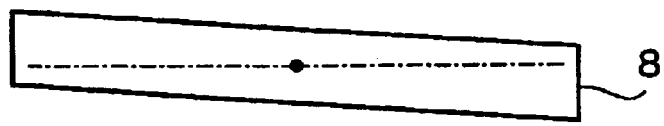
FIG. 24 is another plan view showing where the light shielding plate is observed in a state of being distorted.
Figure 25:
FIG. 25 is a plan view showing another modification of the light shielding plate.
Figure 26:
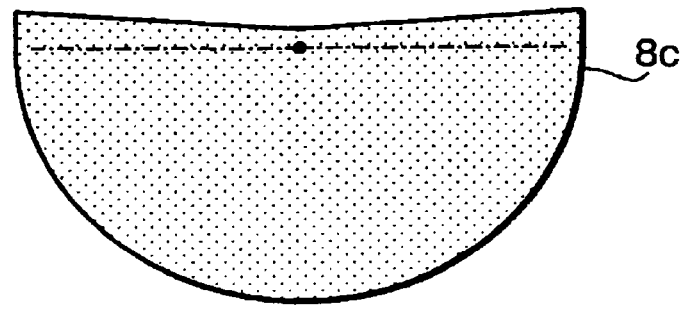
FIG. 26 is a plan view showing another modification of the light shielding plate.

Moreover, in the case where the inspection target optical member 24 includes a cylindrical component (anamorphic lens, cylindrical lens etc.), the refraction power of the inspection target optical member 24 varies depending upon a circumferential direction. Thus, when viewing from the position of the image pick-up device 3, the light shielding plate 8 observed through the inspection target optical member 24 distorts as shown in FIG. 23 and FIG. 24, accompanying rotation of the inspection target optical member 24. In such a case, even if the aforesaid distortion causes, in order to shield a light which transmits through the inspection target optical member 24 and is incident upon the imaging lens 4, a light shielding plate 8b as shown in FIG. 25 may be used. The light shielding plate 8b has a shape which is gradually expanded from the optical axis side toward the outer edge. If the light shielding plate 8b having the aforesaid shape has been employed, it is possible to improve detection accuracy in the vicinity of the optical axis l, and to at least prevent a normal portion from being regarded as a defect portion in the vicinity of the outer peripheral edge. In this case, in place of the light shielding plate 8b, a light shielding plate 8c having a substantially semi-circular shape as shown in FIG. 26 may be used.

Modification of second embodiment

Figure 21:
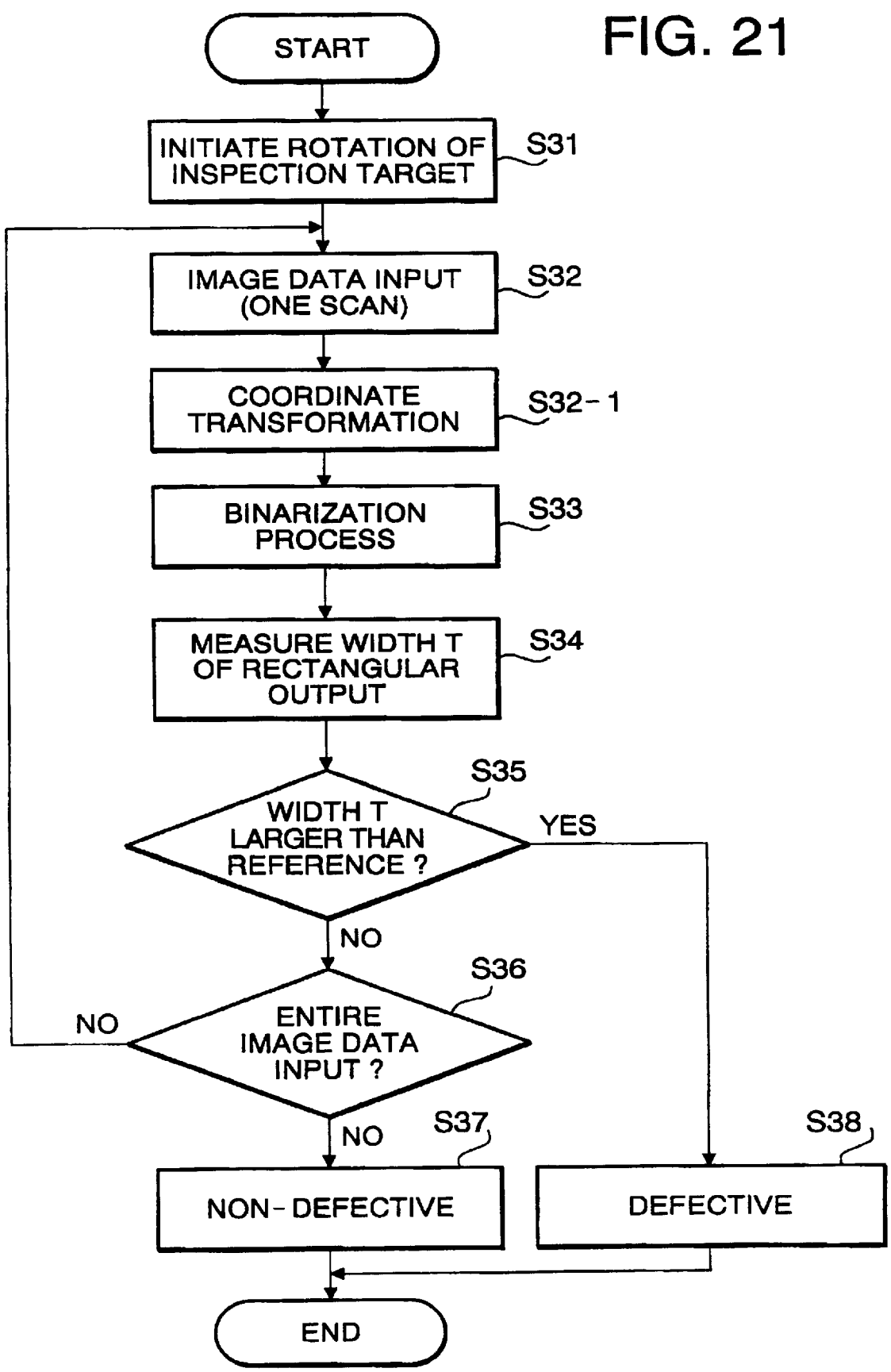
FIG. 21 is a flowchart showing the content of a control process carried out in the image processing unit in a modification of the second embodiment of the present invention.

With this modification, the image processor unit 21 has no image memories 21a and 21b, and a control process by the image processor unit 21 is executed according to a flowchart shown in FIG. 21, as compared with the second embodiment. The control process according to the flowchart of FIG. 21 is the same as the control process of FIG. 13, except for the following matters. Specifically, the binarization process and discrimination process are directly executed with respect to an image data for one line output from the line sensor 5. In the first step S31, after the start, the driving signal is outputted to the driving motor 28, and the inspection target optical member 24 is rotated at a fixed speed. Further, in step S32-1, the polar coordinate system is transferred into the rectangular coordinate system.

Embodiment 3

A third embodiment of the present invention shows an optical member inspection apparatus which is suitable for inspecting a circular lens having a power around an optical axis.

With the aforesaid second embodiment, the line sensor 5 obtains an image of an image inspection region corresponding to the entire area of the inspection target optical member 24 in the diameter direction thereof at one time. However, in this third embodiment, the line sensor 5 obtains an image of an image inspection region which extends from the center of the inspection target optical member 24 to an outer edge thereof at one time. This is because by using a narrow uniform illumination area it is possible to improve the resolution with the use of the line sensor 5 having the same number of pixels. In addition, the process for applying the same numerical calculation to transfer from one coordinate system to another is simplified.

Arrangement of the optical member inspection apparatus

Figure 29:
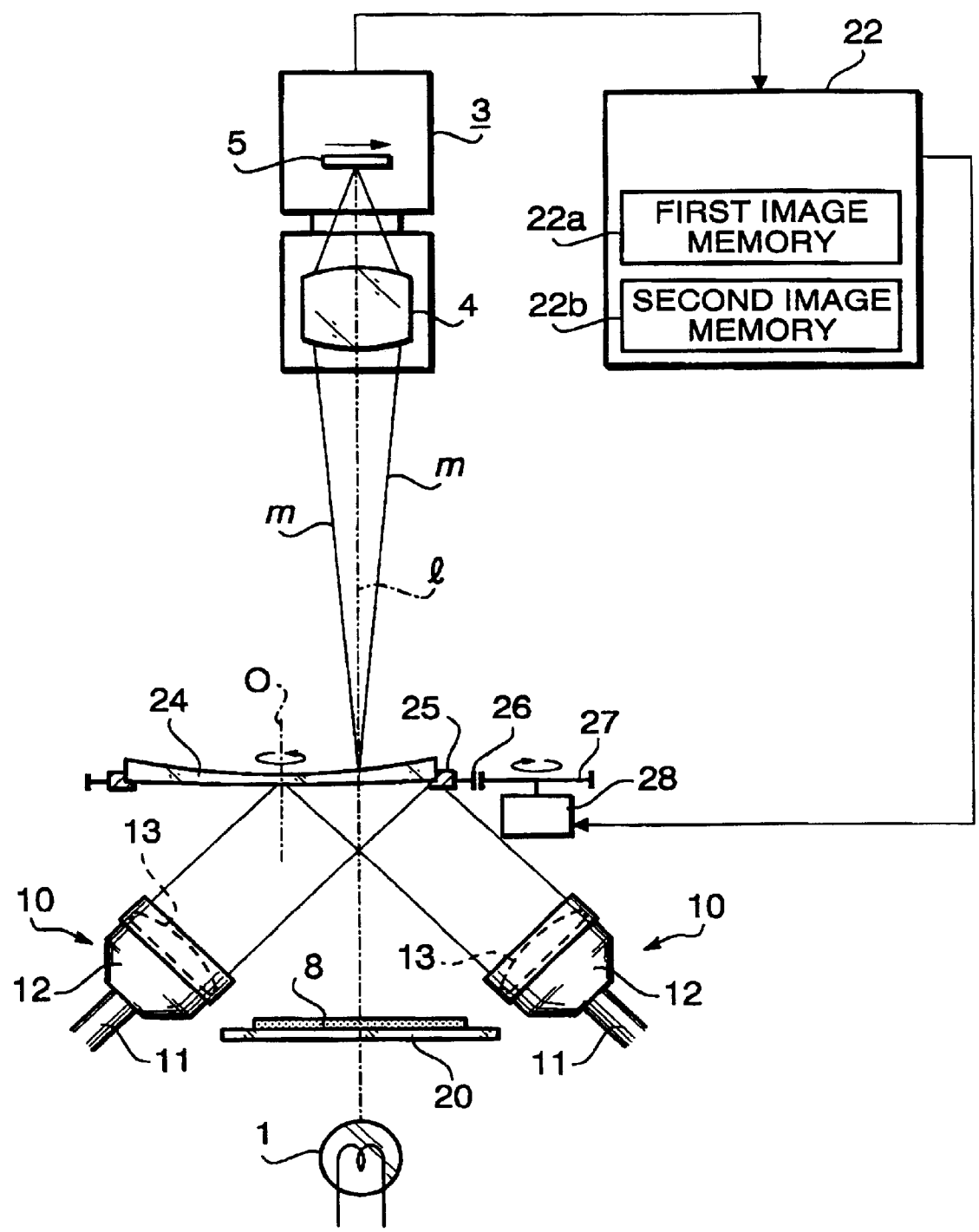
FIG. 29 is a side view schematically showing an optical member inspection apparatus according to a third embodiment of the present invention.

FIG. 29 is a side view schematically showing a construction of an optical member inspection apparatus according to the third embodiment of the present invention. Components common to the first and second embodiments bear common reference numerals.

As shown in FIG. 29, the optical member inspection apparatus comprises an illumination lamp 1, a diffusion plate 20, and an image pick-up device 3, which are arranged on the same optical axis l.

Figure 30:
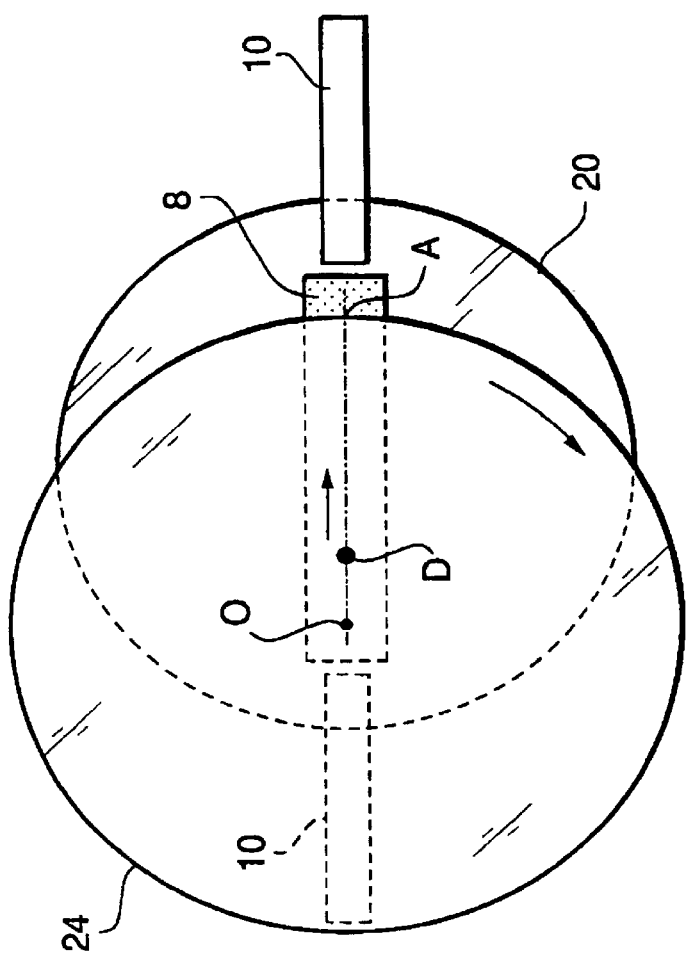
FIG. 30 is a plan view showing an optical member to be inspected from a position of a line sensor shown in FIG. 29.

In this third embodiment, as shown in FIG. 29 and FIG. 30, the center O of the optical axis of the inspection target optical member 24, that is, of the inspection target optical member 24 and the holder 25, is offset parallel to the optical axis l of the imaging lens 4. More specifically, the optical axis l of the imaging lens 4 passes through an intermediate point between the center O and the outer edge of the inspection target optical member 24. That is, in this third embodiment, the driving motor 28, two gears 27 and 26 and the holder 25 are equivalent to a rotating unit for rotating the inspection target optical member 24 around a rotation axis which is offset from the optical axis l of the imaging lens 4. A magnification (i.e., a position of the image pick-up device 3 itself, and a position of the imaging lens 4 to the line sensor 5) of the imaging lens 4, is adjusted so that the image of the area ranging from the center O to the outer edge on the surface of the inspection target optical member 24 is formed on the imaging surface (plane) of the line sensor 5.

Method of discriminating an optical defect

Figure 31:
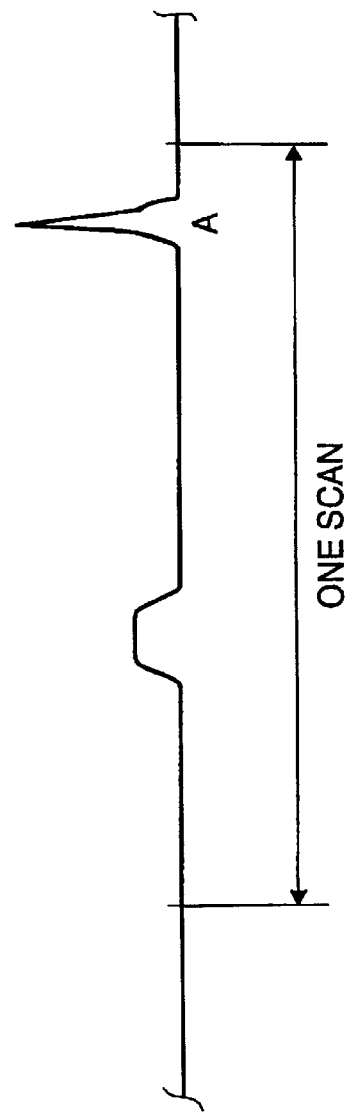
FIG. 31 is a graph showing a luminance distribution of image data outputted from a line snesor in the case where there is an optical defect in the optical member to be inspected.

In this third embodiment, the imaging process (charge storage and scan) by the line sensor 5 is carried out every time the inspection target optical member 24 is rotated by only a unit angle, in synchronism with rotation of the inspection target optical member 24 by the driving motor 28. Then, every time the image capturing by the line sensor 5 is carried out, image data as shown in FIG. 31 is inputted to the image processor unit 22, and is written in a first image memory 22a.

Figure 32A:
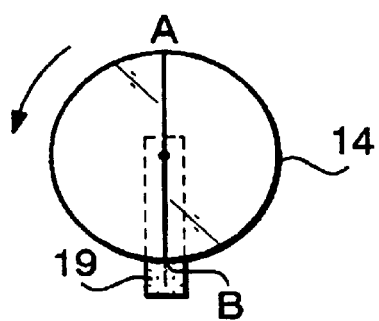
FIG. 32A and FIG. 33A are each a view showing a relationship between relative positions of the light shielding plate, an imaging region and the inspection target optical member, and image data written in a first image memory.
Figure 33A:
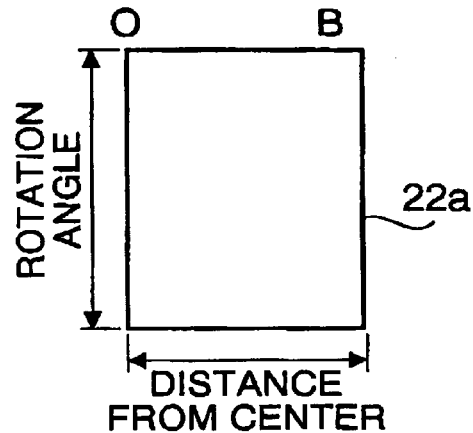
Figure 32B:
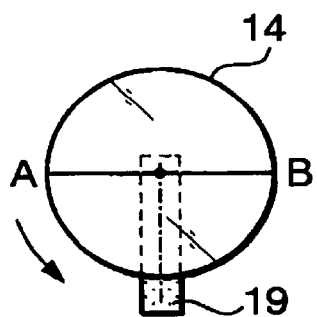
FIG. 32B and FIG. 33B are each a view showing a relationship between relative positions of the light shielding plate, an imaging region and the inspection target optical member, and image data written in the first image memory.
Figure 33B:
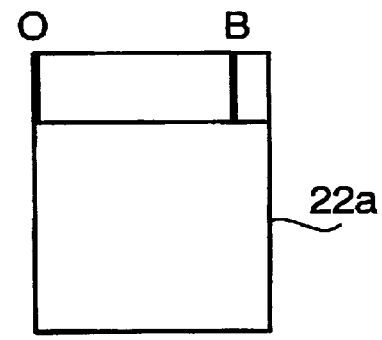
Figure 32C:
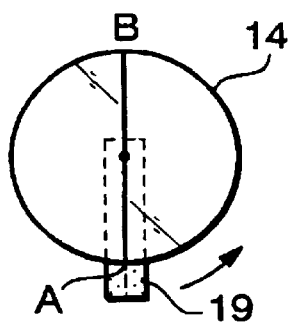
FIG. 32C and FIG. 33C are each a view showing a relationship between relative positions of the light shielding plate, an imaging region and the inspection target optical member, and image data written in the first image memory.
Figure 33C:
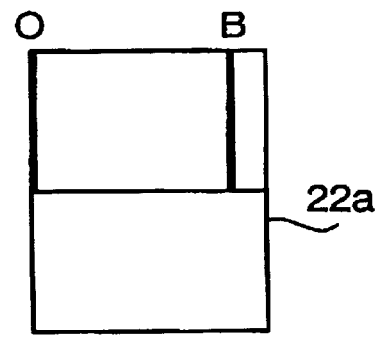
Figure 32D:
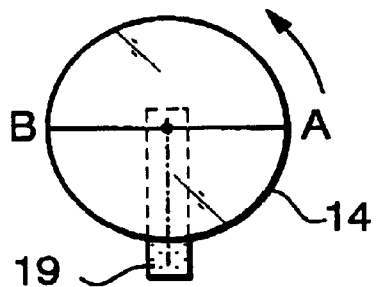
FIGS. 32D and FIG. 33D are each a view showing a relationship between relative positions of the light shielding plate, an imaging region and the inspection target optical member, and image data written in the first image memory.
Figure 33D:
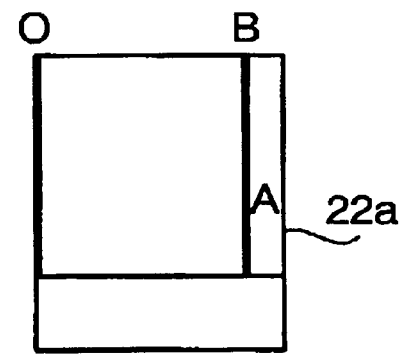
Figure 32E:
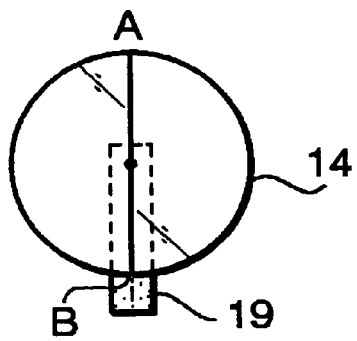
FIG. 32E and FIG. 33E are each a view showing a relationship between relative positions of the light shielding plate, an imaging region and the inspection target optical member, and image data written in the first image memory.
Figure 33E:
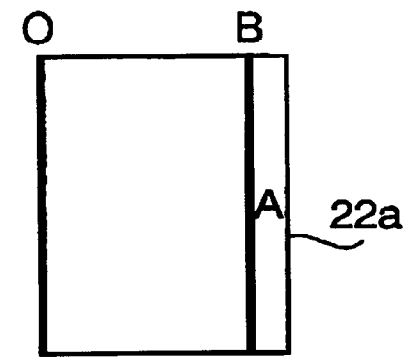

FIG. 32A to FIG. 32E and FIG. 33A to FIG. 33E show a relationship between relative positions of the light shielding plate 8, an imaging inspection region (shown by a chain double dotted line) of the line sensor 5 and the inspection target optical member 24, and the image data written in the first image memory 22a, respectively. More specifically, FIG. 32A and FIG. 33A show the initial state (a point in the imaging area on the peripheral edge of the inspection target optical member 24 at this point of time is set as "B", and a point on the outer edge spaced at an angle of 180° from the point "B" is set as "A"). FIG. 32B and FIG. 33B show a state that the inspection target optical member 24 has been rotated by an angle of 90° in the counterclockwise direction from the initial state. FIG. 32C and FIG. 33C show a state that the inspection target optical member 24 has been rotated by an angle of 180° in the counterclockwise direction from the initial state. FIG. 32D and FIG. 33D show a state that the inspection target optical member 24 has been rotated by an angle of 270° in the counterclockwise direction from the initial state. FIG. 32E and FIG. 33E show a final state that the inspection target optical member 24 has been rotated by an angle of 360° in the counterclockwise direction from the initial state. As shown in each of these figures, when the inspection target optical member 24 is gradually rotated, image data from the line sensor 5 for each scan is written in each line of the first image memory 22a sequentially from the head line thereof.

At the point of time as shown in FIGS. 32E and FIG. 33E, an ordinate of the image data written in the first image memory 22a shows a rotation angle of the inspection target optical member 24 on the basis of a radius connecting between the center (optical axis) O and the point B, and an abscissa thereof shows a distance from the center O of the inspection target optical member 24 to the radius direction thereof. That is, a coordinate system of the data written in the first image memory 22a is a polar coordinate system. Accordingly, the image processor unit 22 converts the image data of the polar coordinate system written in the first image memory 22a into an image data of a rectangular coordinate system, and then, writes the converted image data in the second image memory 22b.

Figure 34:
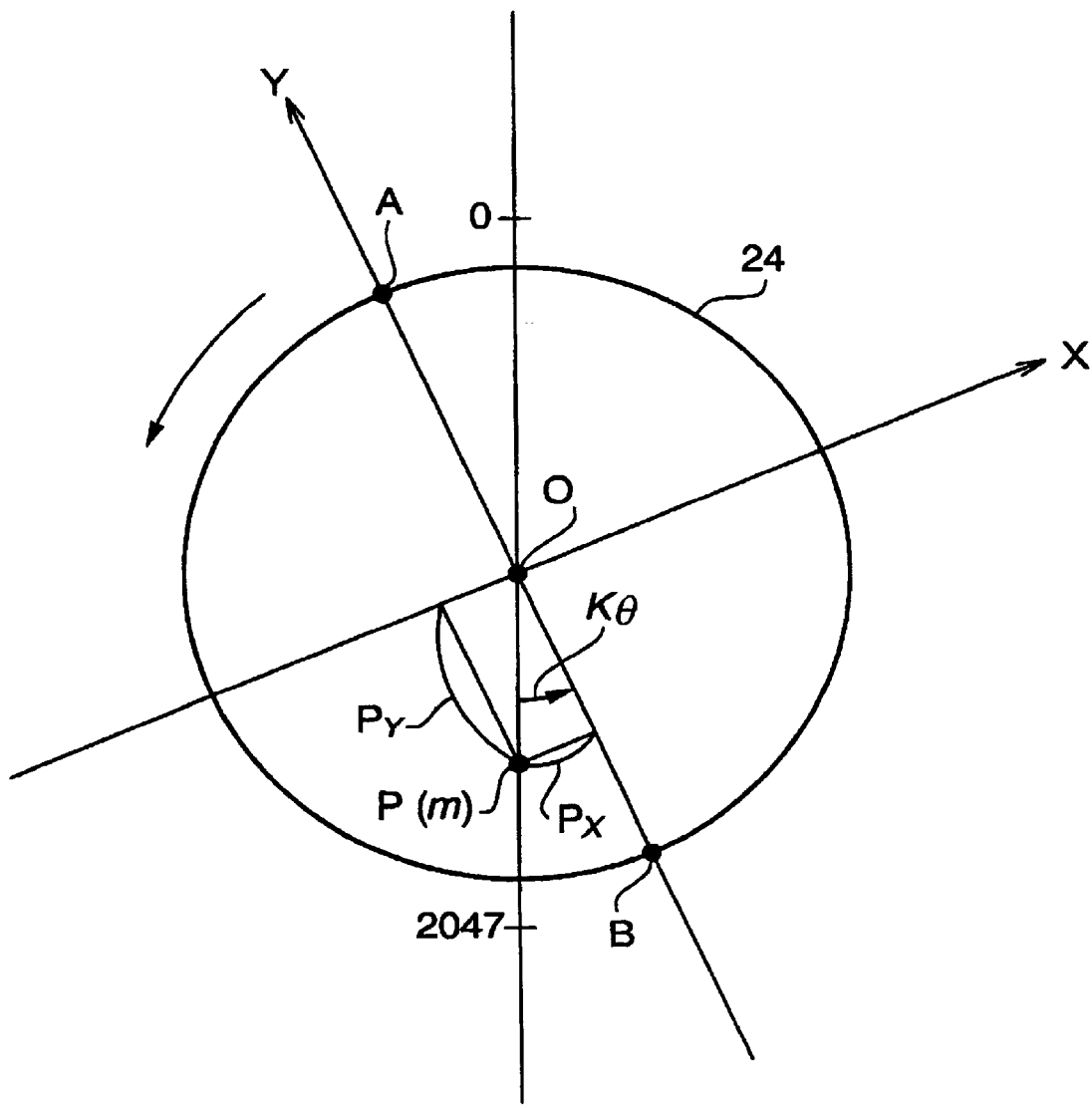
FIG. 34 is a view showing a coordinate transformation method from a polar coordinate system to a rectangular coordinate system.

FIG. 34 is a view showing a coordinate transformation method from the aforesaid polar coordinate system to the rectangular coordinate system, and is the similar method as described in FIG. 18.

FIG. 34 shows a relationship between a local coordinate system defined on the surface of the inspection target optical member 24 and an absolute coordinate system taking the pixel direction of the line sensor 5 as ordinate. In FIG. 34, the local coordinate system defined on the surface of the inspection target optical member 24 sets the optical axis O of the inspection target optical member 24 as the origin 0, and takes the line connecting points A and B on the outer edges of the inspection target optical member 24 as a Y-axis. Further, the local coordinate system takes the line which is perpendicular to the Y-axis and passes through the origin 0 as an X-axis. On the other hand, since a value of each point on the ordinate of the absolute coordinate system corresponds to a scan sequence of each pixel of the line sensor 5, assuming that the resolution (number of pixels) of the line sensor 5 is set as "n", a point "n" have a value of 0 to (n−1). At the point 0, the ordinate of the absolute coordinate system intersects the origin 0 of the local coordinate system.

When the inspection target optical member 24 is rotated, the local coordinate system rotates around the origin 0 in the counterclockwise direction with respect to the ordinate of the absolute coordinate system. At this time, assuming that the number of times of image capturing from the start (number of times of scan) is set as "k", and a rotation angle of the inspection target optical member 24 for one cycle (one scan) of the imaging is set as $\theta$, the polar coordinate of the $m^{th}$ pixel P of the line sensor 5 in the local coordinate system is the point P (m, k$\theta$). Hence, in rectangular coordinates $$Px = m \sin k\theta \tag{5}$$

$$Py = m \cos k\theta \tag{6}$$

Therefore, by making use of these equations (5) and (6), the polar coordinate system can be transferred into the rectangular coordinate system.

As shown in FIG. 35A, the number of pixels n of the line sensor 5 (resolution) is 2048 and assuming 8192 imagings are carried out while the inspection target optical member 24 makes a rotation of 360°, i.e., $\theta$=360/8192. However, the origin (0, 0) of the second image memory 22b is situated at the upper left and therefore a correction needs to be made for shifting the position of origin. More specifically, the second image memory 22b has 4096×4096 pixels. For this reason, the image processor unit 22 must make a correction in a manner of evenly adding 2048 to an X coordinate value obtained from the above equation (5), and evenly adding 2048 to a Y coordinate value obtained from the above equation (6) after reversing the polarity of the Y coordinate value.

That is, the image processor unit 22 executes the following equations (5') and (6') with respect to the pixel of $k^{th}$ line and $m^{th}$ column of the first image memory 22a shown in FIG. 35A.

$$Px = 2048 + m \sin k\theta \tag{5'}$$

$$Py = 2048 - m \cos k\theta \tag{6'}$$

Based on the value Px and Py thus obtained, the pixel of the $Py^{th}$ line and the $Px^{th}$ column of the second image memory 22b shown in FIG. 35B is specified as a pixel after transformation. Then, the data written in the pixel of the $k^{th}$ line and the $m^{th}$ column of the first image memory 22a is written and transferred into the pixel of the $Py^{th}$ line and the $Px^{th}$ column of the second image memory 22b.

In the manner as described above, the image data is written and transferred, and then, the image data stored in the second image memory 22b is equivalent to an image data which is obtained by picking up the image of the inspection target optical member 24 with the use of an area sensor. Thus, an optical defect area of the image data has a proportional relationship to the actual optical defect area regardless of a position of the optical defect. The image processor unit 22 makes a decision whether the inspection target optical member is non-defective or defective on the basis of the image data stored in the second image memory 22b.

Control process

With this third embodiment, in order to make a decision whether the inspection target optical member 24 is non-defective or defective, the control process executed by the image processor unit 22 is carried out according to the flowchart shown in FIG. 20 in the second embodiment. In this case, however, only the equations (5') and (6') above are used for the coordinate transformation in step S24 of the control process.

Operation of third embodiment

With the third embodiment thus constructed, as compared with the second embodiment, using the line sensor 5 having the same number of pixels, the entire length of the imaging region on the inspection target optical member 24 is short so that it is possible to form an image of an optical defect portion in a state of being enlarged. In other words, in the case of inspecting the optical member having a refraction power around the optical axis thereof, it is possible to improve the resolution to the maximum. Further, as described above, the imaging region is narrow, so that it is possible to readily illuminate the imaging region by the illumination lamp 1 and the diffusion plate 20 with a uniform illuminance. Therefore, this contributes to improve the accuracy for detecting the optical defect. Moreover, in the case of converting the data of the polar coordinate system stored in the first image memory 22a into the image data of the rectangular coordinate system, the above equations (5') and (6') are applicable in common to all pixels so that the process can be simplified.

Figure 36:
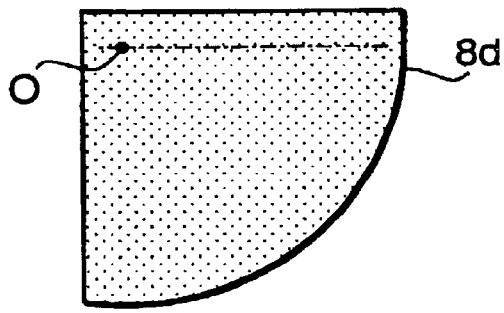
FIGS. 36 is a plan view showing a modification of the light shielding plate.
Figure 37:
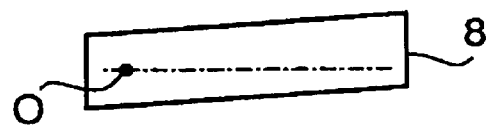
FIG. 37 is a plan view showing where the light shielding plate is observed in a state of being distorted.
Figure 38:
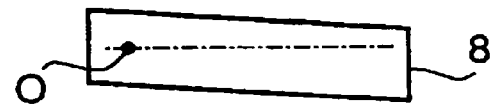
FIG. 38 is a plan view showing where the light shielding plate is observed in a state of being distorted.
Figure 39:
FIG. 39 is a plan view showing another modification of the light shielding plate.
Figure 40:
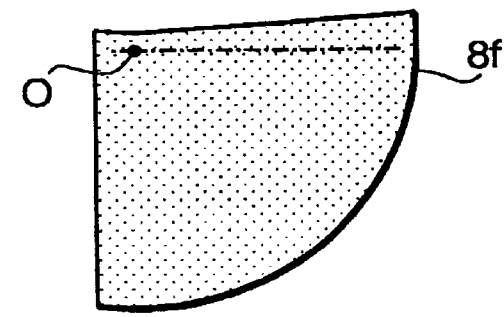
FIG. 40 is a plan view showing another modification of the light shielding plate.

In this third embodiment, in order to detect an optical defect, a light shielding plate 8 as shown in FIGS. 36, 39 and 40 may be used in place of the aforesaid light shielding plate 8, like the second embodiment.

Moreover, in this third embodiment, the control process by the image processor unit 22 may be carried out according to the flowchart shown in FIG. 21.

Embodiment 4

With the fourth embodiment, a pair of line illumination units 41 and 41 are provided in place of the illumination lamp 1 shown in the aforesaid second embodiment shown in and after FIG. 14. The remaining construction and operation of the fourth embodiment is the same as the second embodiment.

Figure 41:
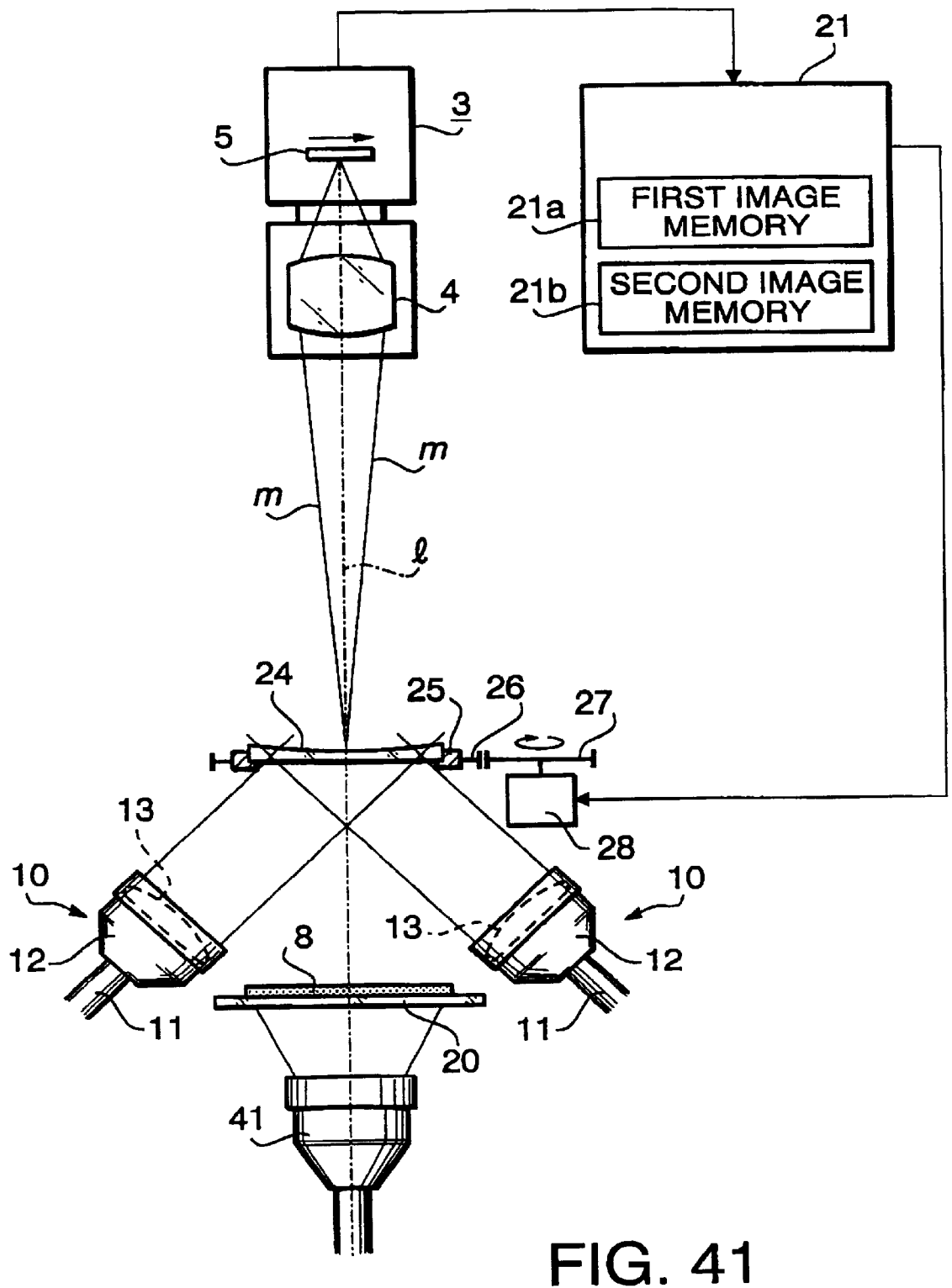
FIG. 41 is a side view schematically showing an optical member inspection apparatus according to a fourth embodiment of the present invention.
Figure 42:
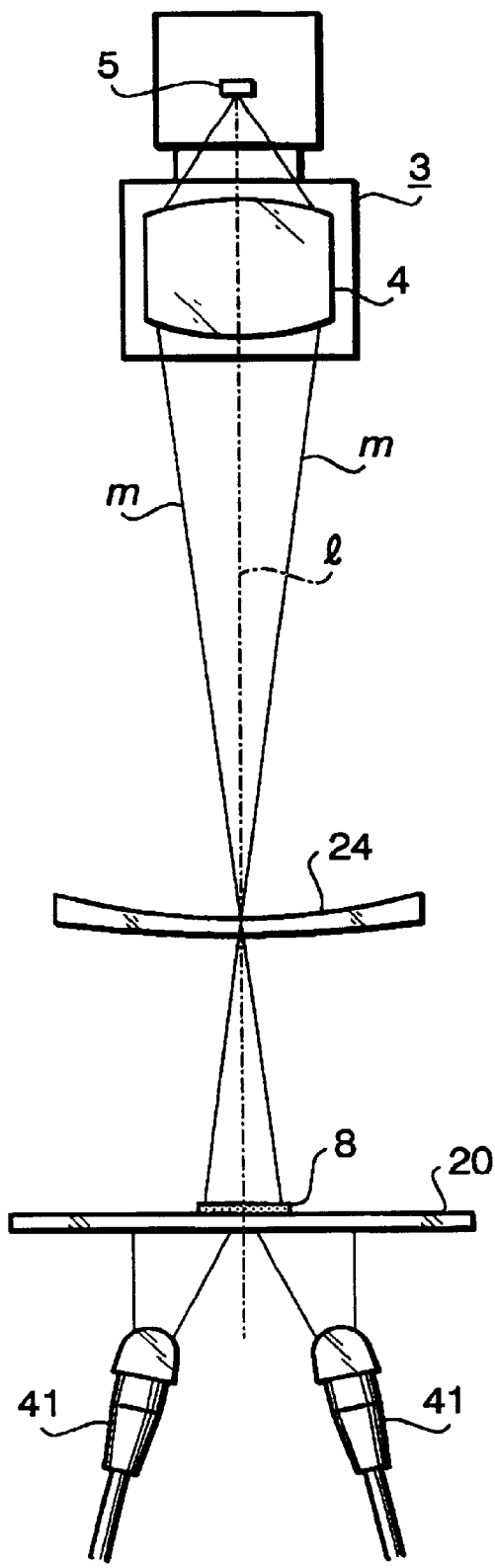
FIG. 42 is a front view showing light ray lines in the case where there is no optical defect in the optical member to be inspected.

FIG. 41 is a side view schematically showing an optical member inspection apparatus according to a fourth embodiment of the present invention. FIG. 42 is a front view showing the light ray lines of FIG. 41.

Figure 43:
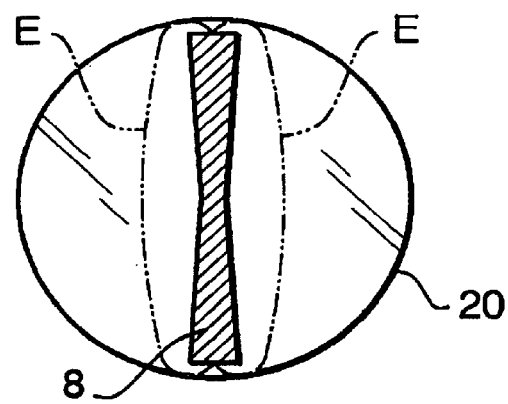
FIG. 43 is a plan view showing the diffusion plate and the light shielding plate shown in FIG. 41.

Each line illumination unit 41 has the same construction as the auxiliary illumination unit 10, except that a lens characteristic is preset such that illumination light emitted therefrom is diverged. As shown in FIG. 41 and FIG. 42, the line illumination units 41 are arranged at a position symmetrical about the optical axis 1 so that a longitudinal direction of their illumination light emitting ends is parallel with the longitudinal direction of the light shielding plate 8. In addition, the illumination light emitting end of each line illumination unit 41 is angled relative to the optical axis 1 so as to be directed to the edge of the light shielding plate 8 in the longitudinal direction thereof. Therefore, as shown in FIG. 43, each line illumination unit 41 independently illuminates a portion, in the longitudinal direction, at and adjacent to the light shielding plate 8 on the diffusion plate 20 (shown by a chain double-dotted line E).

The remaining construction and operation of the fourth embodiment is the same as the second embodiment, and therefore, the details thereof is omitted for simplification.

Modification of fourth embodiment

With this modification, the diffusion plate 20 and the light shielding plate 8 are deleted, and the pair of line illumination units 41 are arranged outside the marginal ray lines m and m of the light that can normally be incident upon each pixel of the line sensor 5.

Figures 44, 45:
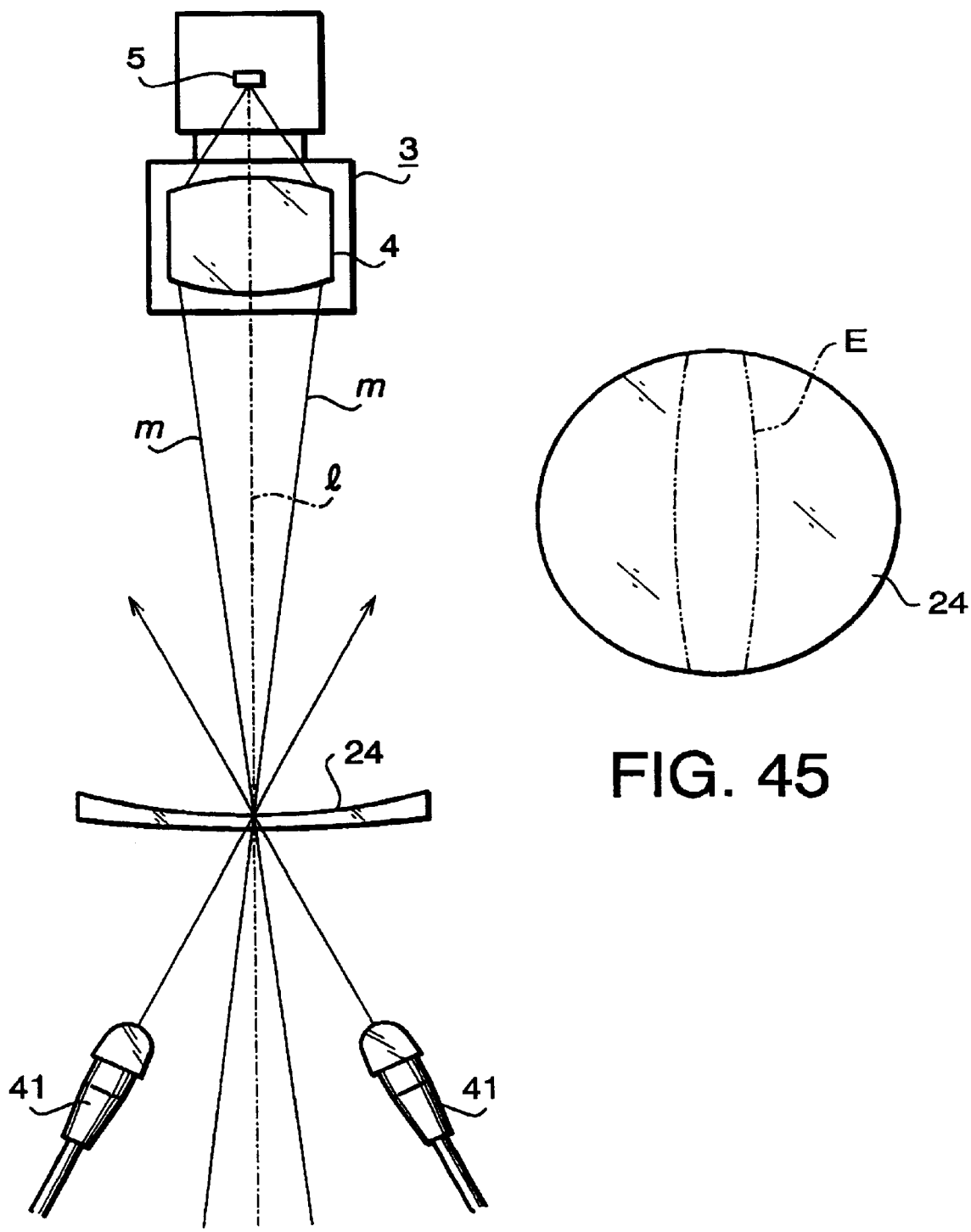
FIG. 44 is a front view schematically showing principal parts of an optical member inspection apparatus according to a modification of the fourth embodiment of the present invention.
FIG. 45 is a plan view showing an optical member to be inspected as shown in FIG. 44.

FIG. 44 is a front view showing light ray lines in an optical member inspection apparatus according to this modification. As shown in FIG. 44, the illumination light is emitted from outside of the marginal ray lines m and m of the light normally incident upon each pixel of the line sensor 5 from the imaging inspection region of the inspection target optical member 24. Therefore, as shown in FIG. 45, an imaging inspection region (shown by a chain double-dotted line E) by the line sensor 5 in the inspection target optical member 24 is illuminated by means of these two line illumination units 41 and 41.

With the aforesaid modified construction, in case the inspection target optical member 24 does not have an optical defect, the illumination light emitted from each line illumination unit 41 is not incident upon the imaging lens 4 after transmission through the inspection target optical member 24. Therefore, the image data from the line sensor 5 is dark. However, in the case where the inspection target optical member 24 has an optical defect, the Illumination light diffuses due to the optical defect, and then, a part of the diffused light is incident upon the imaging lens 4, and thereafter, converges on the line sensor 5. As a result, image data from the line sensor 5 includes a brighter component than the surroundings according to the optical defect.

The other construction and operation are the same as the fourth embodiment.

Embodiment 5

With a fifth embodiment, an optical image of the inspection target optical member 24 is rotated whilst the inspection target optical member 24 itself is not actually rotated. In this fifth embodiment, an image rotator 54 is interposed between the imaging lens 4 and the inspection target optical member 24. In addition, the light shielding plate 8, the diffusion plate 20 and the auxiliary illumination units 10, 10 are integrally constructed so as to be rotated as a unit.

Arrangement of optical member inspection apparatus

Figure 46:
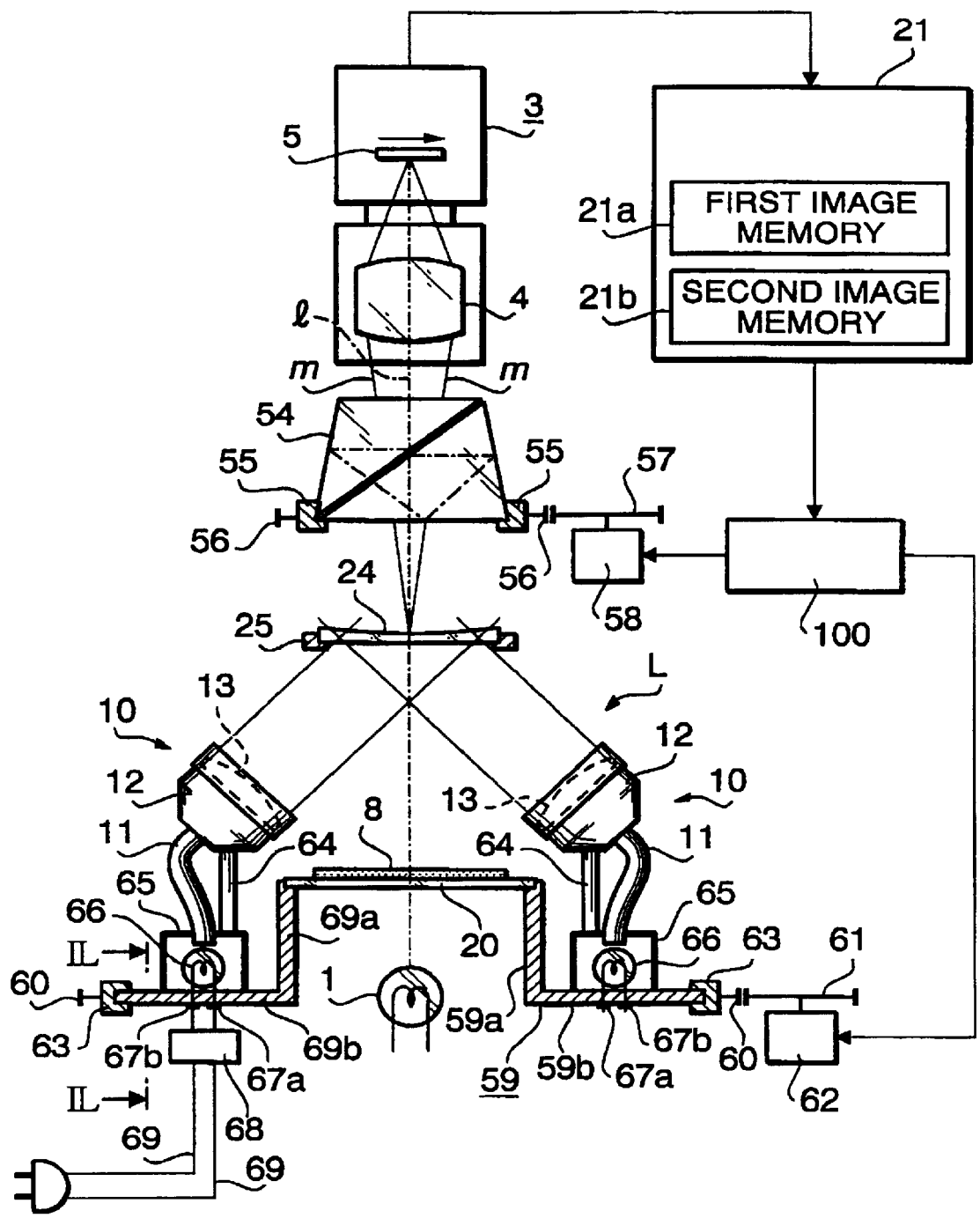
FIG. 46 is a side view schematically showing an optical member inspection apparatus according to a fifth embodiment of the present invention.

FIG. 46 is a side view schematically showing an optical member inspection apparatus according to a fifth embodiment of the present invention. As shown in FIG. 46, the optical member inspection apparatus comprises an illumination unit L, an inspection target holder 25, an image rotator 54, and the image pick-up device 3, which are arranged on the same optical axis 1.

The image rotator 54 is located on an object side of the imaging lens 4. Further, as seen from FIG. 47A of a front view and FIG. 47B of a plan view, the image rotator 54 comprises a trapezium prism which has a rectangular front face 54a, and a square rear face 54e which is composed of four sides, each of which has the same length as a shorter side of the front face 54a. The image rotator 54 is mounted to a frame (not shown) of the optical member inspection apparatus by means of an image rotator holder 55 so as to be rotatable around the same optical axis 1 of the imaging lens 4, which is perpendicular to each center of the front face 54e and the rear face 54a.

The image rotator 54 is divided into two triangular prisms by an interface 54b. The interface 54b intersects the optical axis 1 at an angle of 45° by connecting one shorter side of the front face 54a with the opposing parallel shorter side on the rear face 54e which is situated on the opposite side of the optical axis 1. The interface 54b has a coating so that incident light of an incident angle of approximately 0° is transmitted therethrough and incident light of an incident angle of approximately 45° is reflected. The same coating is also provided on the front face 54a. Moreover, the prism has internal reflection coating provided on the side faces 54c and 54d which connect the shorter sides of the front face 54a to the corresponding sides of the rear face 54e.

With the construction as described above, light which is incident upon the front face 54a of the image rotator in parallel with the optical axis 1 will travel to be reflected at an angle of 90° by means of the interface 54b, and will then travel to the side face 54c to be reflected thereby toward the front face 54a. The light will then be reflected by the front face 54a towards the interface 54b at an incident angle of approximately 0° and therefore passes through to be reflected toward the interface 54b by means of the side race 54d. The light is incident upon the interface 54b at an incident angle of approximately 45° and is therefore reflected toward the rear face 54e to be emitted from the rear upper face 54e parallel to the optical axis 1.

At this time, when viewing the image rotator 54 from the imaging lens 4, the incident light and the emitted light are symmetrical in position with respect to a line Q passing through the aforesaid center of the image rotator 54 and parallel with the shorter side of the lower face 54a.

Figure 47A:
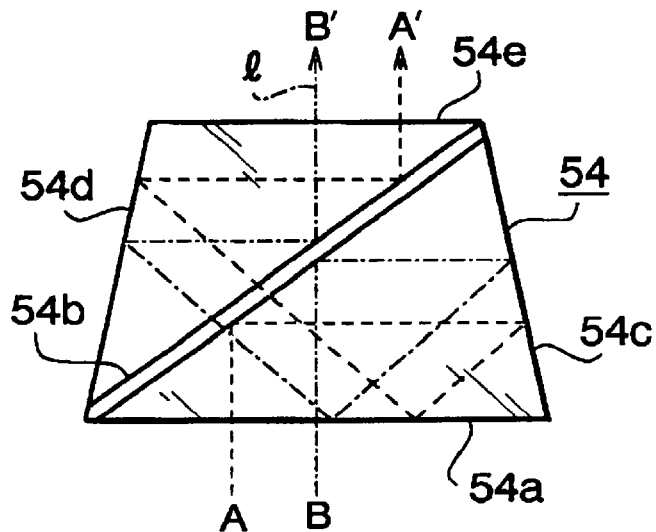
FIG. 47A to FIG. 47C are explanatory views of the image rotator shown in FIG. 46.
Figure 47B:
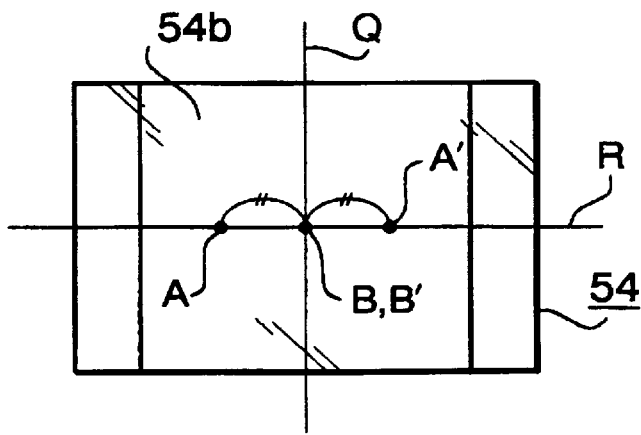
Figure 47C:
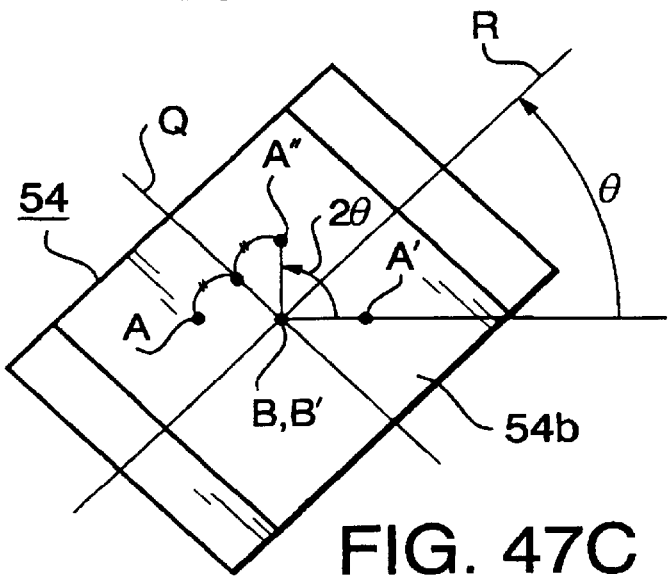

Therefore, as seen from FIG. 47A to FIG. 47C, light which is incident from a point B on the optical axis 1 of the imaging lens 4, transmits through the image rotator 54, and thereafter travels from a point B' on the optical axis 1, regardless of the rotational position of the image rotator 54.

As shown in FIG. 47A and FIG. 47B, light which is incident from a point A (a point exists on a line R passing through the center of the image rotator 54 parallel with the longer side of the front face 54a, and is shifted from the optical axis 1 in a direction parallel with the longer side of the lower face 54a), is transmitted through and exits from the image rotator at a point A' which is symmetrical with respect to the optical axis 1 when viewed from the imaging lens 4.

As shown in FIG. 47C, in the case where the point A is situated at a position other than the points described above, the light therefrom transmits through the image rotator 54, and thereafter, exits from a point A" which is symmetrical with respect to the line Q when viewed from the imaging lens 4.

As a result, a segment A-B is observed at a position A'-B', as shown in FIG. 47B when viewed from the imaging lens 4 in the case where the image rotator 54 is situated at a rotational position such that the line Q and the segment A-B are perpendicular to each other. When the image rotator 54 is rotated by an angle of θ, the segment A-B is rotated by an angle of 2θ, at twice the angular velocity, and is then observed at a position indicated as A"-B' as shown in FIG. 47C. In other words, when the image rotator 54 makes a half rotation around the optical axis 1, an image observed through the image rotator 54 has made one rotation in the same direction.

The image rotator holder 55 has a cylindrical outer peripheral surface around the optical axis 1, and is embedded in a side peripheral edge of the front face 54a of the image rotator 54. The outer peripheral surface of the image rotator holder 55 is formed integrally with an annular gear 56. The annular gear 56 engages with a pinion gear 57 attached to a drive shaft of an image rotator driving motor (pulse motor) 58. Thus, when the image rotator driving motor rotates the drive shaft thereof, the image rotator 54 is rotated via the two gears 57 and 56. That is, the image rotator holder 55, the two gears 56 and 57, and the image rotator driving motor 58 constitute a second rotating mechanism for rotating the image rotator 54 so that the shadow of the light shielding plate 8 formed by the imaging lens 4 always covers the line sensor 5.

The inspection target optical member 24 is a concave lens which has been subjected to a centering process. This inspection target optical member 24 is held by means of an inspection target holder 25 which is fixed on a frame (not shown) of the optical member inspection apparatus. Furthermore, the inspection target optical member 24 is placed so as to be coaxial with the optical axis 1 on the opposite side to the imaging lens 4 via the image rotator 54.

By use of the aforesaid function of the image rotator 54, the image of the image inspection region on the diameter in the right and left direction of FIG. 46 of the inspection target optical member 24 is captured by means of the line sensor 5 when the line Q of the image rotator 54 is perpendicular to the sheet of FIG. 46 (hereinafter, the position of the image rotator 54 at this point in time is referred to as "initial position"). Further, from this state, when the image rotator 54 is rotated by an angle of 45 in the counterclockwise direction viewed from the image pick-up device 3, the image on the diameter in the direction perpendicular to the sheet of FIG. 46 in the inspection target optical member 24 is obtained by means of the line sensor 5.

The illumination unit L is composed of the diffusion plate 20 and the illumination lamp 1, which are arranged on the side of the inspection target optical member 24 remote from the imaging lens 4 but on the optical axis 1 of the imaging lens 4. A strip-like light shielding plate 8 is stuck onto the surface of the diffusion plate 20. A diffusion plate holder 59 holds the diffusion plate 20 and is rotated around the optical axis 1, and a pair of auxiliary illumination units 10 and 10 are provided outside opposite ends of the light shielding plate 8 on the diffusion plate holder 59.

The diffusion plate holder 59, which surrounds the illumination lamp 1, is composed of a tubular portion 59a which is coaxial with the optical axis 1 of the imaging lens 4. An annular flange portion 59b coaxially extends in the circumferential direction thereof from the lower end of the tubular portion 59a whilst at the upper end of the tubular portion 59a an opening is provided to which the disc-like diffusion plate 20 is attached having a diameter larger than the inspection target optical member 24.

The diffusion plate holder 59 is supported by a frame (not shown) of the optical member inspection apparatus so as to be freely rotatable around the optical axis 1 of the imaging lens 4.

Thus, the diffusion plate 20 is positioned on the opposite side of the inspection target optical member 24 to the image rotator 54 and is rotated coaxially about the optical axis 1 of the imaging lens 4 by means of the diffusion plate holder 59.

Moreover, the light shielding plate 8 is initialized so that the longitudinal direction thereof is parallel with the pixel arrangement of the line sensor 5 when the image rotator 54 is situated at the initial position.

Two auxiliary illumination units 10 and 10 are fixed on the surface of the flange portion 59b of the diffusion plate holder 59 at a position corresponding to the outside of the both ends of the light shielding plate 8 in the longitudinal direction thereof. Each auxiliary illumination unit 10 is composed of a light box fixed on the flange portion 59b, an auxiliary illumination lamp 66 housed in the light box 65, an optical fiber bundle 11 for directing the auxiliary illumination light emitted from the auxiliary illumination lamp 66 to the outside of the light box 65, a divergence restricting frame 12 which is attached to an emitting end of the optical fiber bundle 11 and is fixed above the light box 65 by means of a stay 64, and a collimator lens 13 attached to an emitting end of the divergence restricting frame 12.

Figure 48:
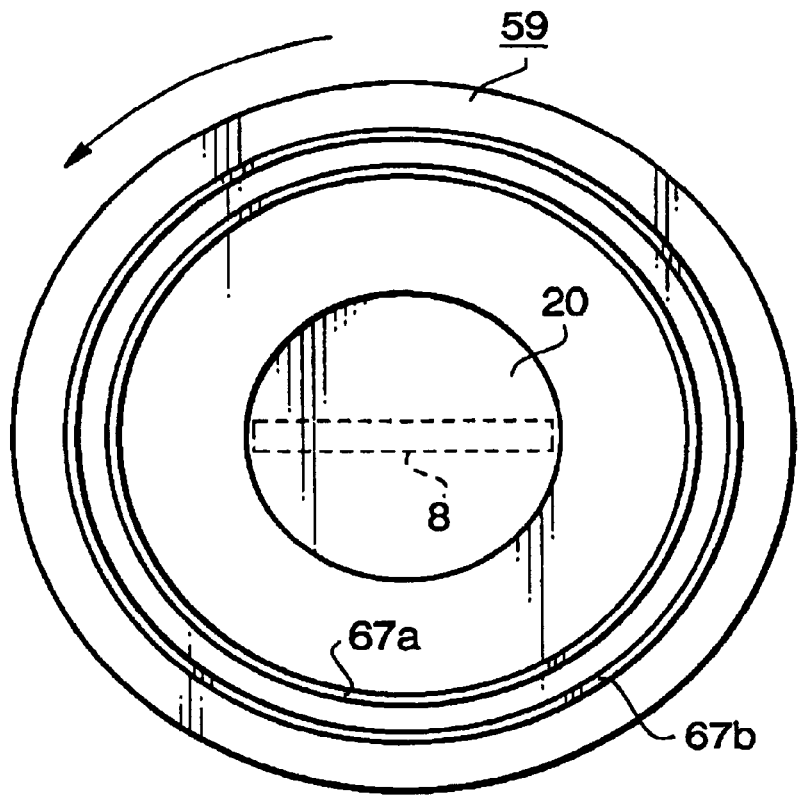
FIG. 48 is a rear view showing the diffusion holder shown in FIG. 46.
Figure 49:
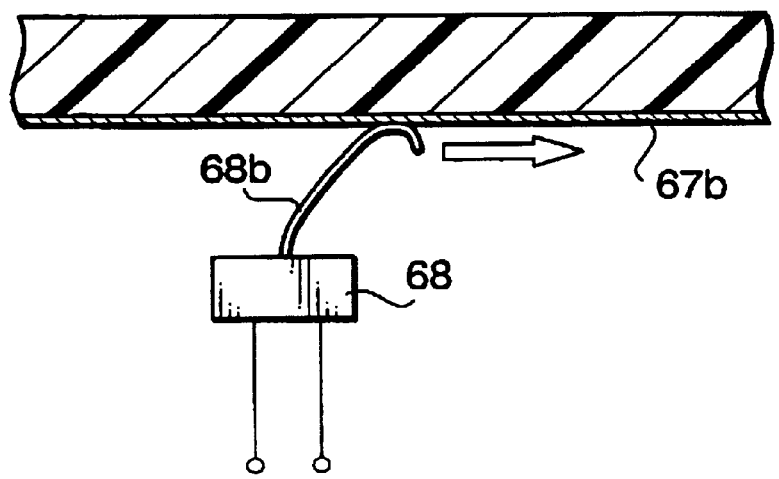
FIG. 49 is a partial sectional view cut along a line II—II of FIG. 46.

A lead wire for supplying current to the respective auxiliary illumination lamps 66 and 66 extends through the flange portion 59b of the diffusion plate holder 59, and contacts respective annular electrodes 67a and 67b as shown in FIG. 48. These annular electrodes 67a and 67b are arranged coaxially with each other on the bottom side of the flange portion 59b. As shown in FIG. 49, which is a partial sectional view cut along a line II—II of FIG. 46, each annular electrode 67a, 67b is always in slidable contact with either of a pair of brushes 68a and 68b which are provided on a brush retaining portion 68 fixed on a frame (not shown) of the optical member inspection apparatus. Thus, when electric cables 69 and 69, connected to these brushes 68a and 68b, are connected to a power source (not shown), electric current is supplied to each auxiliary illumination lamp 66 and 66 via the sliding contact of these brushes 68a and 68b with the annular electrodes 67a and 67b. Therefore, regardless of the rotational position of the diffusion plate holder 59, an auxiliary illumination light is always emitted from respective auxiliary illumination units 10 and 10, and is irradiated to the inspection target optical member 24 from the outside of both ends of the light shielding plate 8.

An annular rim 63 is provided on the periphery of the flange portion 59b of the diffusion plate holder 59. An outer peripheral surface of the rim 63 is formed integrally with an annular gear 60. The annular gear 60 engages with a pinion gear 61 attached to a driving shaft of a light shielding plate driving motor (pulse motor) 62. Thus, when the driving shaft of the light shielding plate driving motor 62 is rotated, the diffusion plate 20, the light shielding plate 8 and respective auxiliary illumination units 10 and 10 are rotated via the two gears 60 and 61. In other words, the diffusion plate 20, diffusion plate holder 59, rim 63, two gears 60 and 61 and the light shielding plate driving motor 62 constitute a first rotating mechanism for rotating the light shielding plate 8 around the optical axis 1.

A motor driving circuit 100 functions as a part of the first and second rotating mechanisms. When the motor driving circuit 100 receives a control signal from the image processor unit 21, the motor driving circuit 100 supplies a driving pulse to the light shielding plate driving motor 62 for rotating the diffusion plate 20 and the light shielding plate 8 in the counterclockwise direction viewed from the image pick-up device 3 at a first fixed speed. The motor driving circuit 100 further supplies a driving pulse to the image rotator driving motor 58 for rotating the image rotator 54 in the counterclockwise direction viewed from the image pick-up device 3 at a second fixed speed which is a half of the first fixed speed.

As described above, the light shielding plate 8 is initialized so that the longitudinal direction thereof becomes parallel with the pixel row of the line sensor 5 when the image rotator 54 is situated in the initial position. Moreover, the diffusion plate 20 and the light shielding plate 8 are rotated in the counterclockwise direction viewed from the image pick-up device 3 at the first fixed speed, while the image rotator 54 is rotated in the counterclockwise direction viewed from the image pick-up device 3 at the second fixed speed which is a half of the first fixed speed.

Thus, when viewed from the image pick-up device 3, due to the aforesaid arrangement and the function of the image rotator 54, the light shielding plate 8 appears to be stationary in that the longitudinal direction thereof is aligned to the pixel row direction of the line sensor S. Then, the inspection target optical member 24 is observed as if it were rotated in the counterclockwise direction at the first fixed speed. Unless the inspection target optical member 24 has an optical defect, the shadow of the light shielding plate 8 always covers the line sensor 5. Further, the imaging inspection region (i.e., the diameter direction region imaged on the pixel row of the line sensor 5) is relatively rotated in the clockwise direction with respect to the inspection target optical member 24.

The image capturing (charge storage and scan) process by the line sensor 5 is carried out every time the inspection target optical member 24 viewed from the image pick-up device 3 is relatively rotated by a unit angle, in synchronism with rotation of the diffusion plate 20, the light shielding plate 8 and the inspection target optical member 24 and the image rotator 54 by the driving motors 58 and 62. Then, every time the image capturing process by the line sensor 5 is carried out, the aforesaid image data as shown in FIG. 15A of the second embodiment is inputted to the image processor unit 21, and is written in the first image memory 21a. Further, the same coordinate transformation as the second embodiment is carried out, followed by a decision according to the aforesaid control process as shown in FIG. 20 of the second embodiment.

Modification of the fifth embodiment

With this modification compared to the fifth embodiment, the image processor unit 21 does not have image memories 21a and 21b, and the control process by the image processor unit 21 is executed according to the flowchart shown in FIG. 21 of the second embodiment.

In the above, different embodiments are disclosed for effectively scanning the optical member through the shadow region by relative movement between the optical member and that shadow region. It will be appreciated that the term shadow region should be interpreted to encompass a region of reduced light intensity compared with that of the illumination means and not necessarily a region with a complete absence of light.

The present disclosure relates to subject matters contained in Japanese Patent Applications No. EEI 9-50760 and No. HEI 9-50761, both filed on Mar. 5, 1997, which are expressly incorporated herein by reference in their entireties.

What is claimed is:

1. An optical member inspection apparatus for detecting an optical defect of an inspection target optical member, the apparatus comprising:

an imaging lens;

a line sensor arranged at a position conjugate to said inspection target optical member with respect to said imaging lens;

an illuminator for illuminating said inspection target optical member;

a light shielding member interposed between said inspection target optical member and said illuminator, for preventing direct illumination of said line sensor by said illuminator by shielding an optical path of light which would be incident upon said line sensor after direct transmission from said illuminator through said inspection target optical member, so that an optical image obtained by said line sensor is formed from light from said illuminator diffused by said optical defect;

a numerical system which determines a numerical value for said optical image obtained by said line sensor, said numerical value being indicative of said optical defect of said inspection target optical member; and a discrimination system which makes a decision whether said numerical value exceeds a predetermined discrimination reference value.

2. The optical member inspection apparatus according to claim 1, wherein said illuminator includes a diffusion plate, provided on an opposite side of said light shielding member to said imaging lens, for diffusing an illumination light toward said inspection target optical member.

3. The optical member inspection apparatus according to claim 2, wherein said line sensor has a scanning direction which extends in a fixed direction perpendicular to an optical axis of said imaging lens, and wherein said light shielding member has a shape extending in said fixed direction.

4. The optical member inspection apparatus according to claim 3, wherein magnification of the imaging lens is adjusted so that the image of the entire width of said inspection target optical member is obtained by means of said line sensor.

5. The optical member inspection apparatus according to claim 4, wherein said light shielding member has a strip-like shape.

6. The optical member inspection apparatus according to claim 3, which further comprises a transfer unit to move said inspection target optical member in a direction perpendicular to said scanning direction of said line sensor, and wherein said line sensor captures an image of said inspection target optical member at different positions, and outputs an image data for each one line.

7. The optical member inspection apparatus according to claim 3, which further comprises an auxiliary illumination unit which illuminates said inspection target optical member from a side of said light shielding member in said fixed direction.

8. The optical member inspection apparatus according to claim 6, wherein said numerical system reconstructs an image data corresponding to the entire inspection target optical member on the basis of the image data for each one line outputted from said line sensor, and measures a number of pixels having a luminance larger than a predetermined threshold value in said image data.

9. The optical member inspection apparatus according to claim 3, which further comprises a rotating unit which rotates said inspection target optical member around an optical axis of said imaging lens, wherein magnification of the imaging lens is adjusted so that the image of the entire region of said inspection target optical member in a diameter direction thereof is obtained by means of said line sensor, and wherein said line sensor captures an image of said inspection target optical member at different positions, and outputs an image data for each one line.

10. The optical member inspection apparatus according to claim 3, which further comprises a rotating unit which rotates said inspection target optical member around a rotating axis offset from said optical axis of said imaging lens, wherein magnification of the imaging lens is adjusted so that the image of a region ranging from said rotating axis to an outer edge of said inspection target optical member is captured by means of said line sensor, and wherein said line sensor captures an image of said inspection target optical member at different positions, and outputs an image data for each one line.

11. The optical member inspection apparatus according to claim 10, wherein said numerical system measures a length of a portion of image data having a luminance larger than a predetermined threshold value in said image data for each one line outputted from said line sensor.

12. The optical member inspection apparatus according to claim 10, wherein said numerical system reconstructs an image data of a polar coordinate system corresponding to the entire inspection target optical member on the basis of the image data for each one line outputted from said line sensor, converts said image data of polar coordinate system into an image data of a rectangular coordinate system, and measures a number of pixels having a luminance larger than a predetermined threshold value in said image data of rectangular coordinate system.

13. The optical member inspection apparatus according to claim 10, wherein said inspection target optical member comprises a lens.

14. The optical member inspection apparatus according to claim 13, wherein said rotating unit rotates said lens around an optical axis thereof.

15. The optical member inspection apparatus according to claim 14, wherein said light shielding member has a strip-like shape which is gradually expanded from a portion intersecting said optical axis of said lens to an end portion thereof.

16. An optical member inspection apparatus for detecting an optical defect of an inspection target optical member, comprising:

an imaging lens;

an image rotator which is arranged on an object side of said imaging lens so as to be freely rotatable around an optical axis of said imaging lens;

a fixing member for fixing said inspection target optical member on said optical axis on a side opposite to said imaging lens via said image rotator;

a line sensor which is arranged on a position conjugate to said inspection target optical member fixed on said fixing member with respect to said imaging lens;

a diffusion plate which is arranged on a side opposite to said image rotator via said inspection target optical member fixed on said fixing member, and diffuses an illumination light toward said inspection target optical member;

a light shielding member which is interposed between said diffusion plate and said inspection target optical member, and shields an optical path of an illumination light which is incident upon said line sensor after transmitting through said inspection target optical member and being incident upon said imaging lens;

a first rotating mechanism for rotating said light shielding member around said optical axis;

a second rotating mechanism for rotating said image rotator so that a shadow of said light shielding member formed by said imaging lens always covers said line sensor, in synchronism with rotation of said light shielding member by said first rotating mechanism;

numerical system which determines a numerical value for an optical image obtained by said line sensor; and discrimination system which makes a decision whether said numeral value exceeds a predetermined discrimination reference value.

17. The optical member inspection apparatus according to claim 16, wherein magnification of the imaging lens is adjusted so that the image of the entire region of said inspection target optical member in a diameter direction intersecting said optical axis is obtained by means of said line sensor.

18. The optical member inspection apparatus according to claim 16, wherein said light shielding member has a strip-like shape which is extended to a direction perpendicular to said optical axis of said imaging lens.

19. The optical member inspection apparatus according to claim 16, wherein said image rotator is constructed in a manner that when said image rotator is rotated by a predetermined angle around said optical axis, a position of a ray emitted from said image rotator is rotated by a twice angle of said predetermined angle around said optical axis.

20. The optical member inspection apparatus according to claim 19, wherein said second rotating mechanism rotates said image rotator at a speed which is a half of a rotating speed of said light shielding member by said first rotating mechanism.

21. The optical member inspection apparatus according to claim 16, wherein said numerical system measures a length of a portion of image data having a luminance larger than a predetermined threshold value in said image data for each one line outputted from said line sensor.

22. The optical member inspection apparatus according to claim 16, wherein said numerical system reconstructs an image data of a polar coordinate system corresponding to the entire inspection target optical member on the basis of the image data for each one line outputted from said line sensor, converts said image data of polar coordinate system an image data of a rectangular coordinate system, and measures a number of pixels having a luminance larger than a predetermined threshold value in said image data of rectangular coordinate system.

23. The optical member inspection apparatus according to claim 18, wherein said inspection target optical member comprises a lens.

24. The optical member inspection apparatus according to claim 23, wherein said light shielding member has a strip-like shape which is gradually expanded from a portion intersecting said optical axis of said lens to an end portion thereof.

25. The optical member inspection apparatus according to claim 17, which further includes an auxiliary illumination unit which is rotated around said optical axis by means of said first rotating mechanism together with said light shielding member, and illuminates said inspection target optical member from the vicinity of an end of side of said light shielding member.

26. The optical member inspection apparatus according to claim 16, wherein said second rotating mechanism rotates said image rotator in a reverse direction to said rotating direction of said light shielding member by said first rotating mechanism.

* * * * *